United States Patent
Nazareth et al.

(10) Patent No.: US 12,385,001 B2
(45) Date of Patent: *Aug. 12, 2025

(54) SYSTEMS, METHODS AND APPARATUS FOR THE AUTOMATED CULTURE OF CELLS

(71) Applicant: STEMCELL TECHNOLOGIES CANADA INC., Vancouver (CA)

(72) Inventors: Emanuel Nazareth, Vancouver (CA); Eric Jervis, Vancouver (CA); Martin O'Keane, Vancouver (CA); Carrick Faris, Vancouver (CA)

(73) Assignee: StemCell Technologies Canada Inc., Vancouver (CA)

( * ) Notice: Subject to any disclaimer, the term of this patent is extended or adjusted under 35 U.S.C. 154(b) by 1216 days.

This patent is subject to a terminal disclaimer.

(21) Appl. No.: 17/253,838

(22) PCT Filed: Jun. 19, 2019

(86) PCT No.: PCT/CA2019/050859
§ 371 (c)(1),
(2) Date: Dec. 18, 2020

(87) PCT Pub. No.: WO2019/241885
PCT Pub. Date: Dec. 26, 2019

(65) Prior Publication Data
US 2021/0317399 A1    Oct. 14, 2021

Related U.S. Application Data

(60) Provisional application No. 62/686,962, filed on Jun. 19, 2018.

(51) Int. Cl.
*C12M 1/36* (2006.01)
*C12M 1/00* (2006.01)
(Continued)

(52) U.S. Cl.
CPC ............ *C12M 41/48* (2013.01); *C12M 23/20* (2013.01); *C12M 23/48* (2013.01); *C12M 33/04* (2013.01);
(Continued)

(58) Field of Classification Search
CPC ....... C12M 41/48; C12M 47/02; G01N 35/00; C12N 5/0696
See application file for complete search history.

(56) References Cited

U.S. PATENT DOCUMENTS 9,365,821 B2 * 6/2016 Bhatia ................ G01N 33/5073
10,184,104 B2 * 1/2019 Lianides ................ C12M 23/38
(Continued)

FOREIGN PATENT DOCUMENTS

CA    2607217 A1    11/2006
CA    2920667 A1    2/2015

OTHER PUBLICATIONS

Jain et al., The Complete Automation of Cell Culture: Improvements for High-Throughput and I-73 High-Content Screening, J. Biomolecular Screening, Sep. 1, 2011, vol. 16, No. 8, pp. 932-939.
(Continued)

*Primary Examiner* — Emily C Terrell
*Assistant Examiner* — Ahmed A Nasher
(74) *Attorney, Agent, or Firm* — Smart & Biggar LP

(57) ABSTRACT

Systems and methods for the automated culture of cells and apparatus and methods for dissociating one or more colonies in a culture of cells are described. The automated systems include at least an imaging module, a pipette module, a handling module, and optionally a stage module. Coordinated operation of the foregoing modules is effected by at least one processor based on one or more characteristics of the culture of cells calculated from one or more images captured at a first time point and at one or more subsequent
(Continued)

time points. The apparatus includes a mounting surface, having one or more impact bumpers, connected to a rotatable drive, a platform rotatable dependently or independently of the drive, and one or more impact brackets connected to the platform and collidable with the one or more impact bumpers to transmit a dissociative force to a culture of cells in a cell culture vessel upon the platform.

21 Claims, 19 Drawing Sheets

(51) Int. Cl.
    *C12M 1/26*     (2006.01)
    *C12M 1/34*     (2006.01)
    *C12M 3/00*     (2006.01)
    *C12N 5/074*     (2010.01)

(52) U.S. Cl.
    CPC ............ *C12M 41/36* (2013.01); *C12M 41/44* (2013.01); *C12M 41/46* (2013.01); *C12N 5/0696* (2013.01)

(56) References Cited

U.S. PATENT DOCUMENTS

2014/0363467 A1* 12/2014 Stice .................. A01K 67/0275
    800/19
2015/0166964 A1* 6/2015 Noggle .................. C12M 23/12
    435/377
2018/0282682 A1* 10/2018 Pebay .................... C12M 41/48
2019/0338237 A1* 11/2019 Tanabe ................... C12M 29/00

OTHER PUBLICATIONS

Konagaya et al., Long-term maintenance of human induced pluripotent stem cells by automated I-73 cell culture. Scientific Reports, Nov. 17, 2015, vol. 5, Article No. 16647.

Jaccard et al., Automated method for the rapid and precise estimation of adherent cell I-73 culture characteristics from phase contrast microscopy images. Biotechnol Bioeng, Mar. 1, 2014, vol. III, No. 3, pp. 504-517.

Daniszewski et al., Automated Cell Culture Systems and Their Applications to Human Pluripotent Stem Cell Studies, SLAS Technol., Aug. 2018, vol. 23, No. 4, pp. 315-325, Epub Jun. 2, 2017.

Kempner and Felder, A review of cell culture automation, Journal of the Association for Laboratory Automation (JALA), Apr. 1, 2002, vol. 7, No. 2, pp. 56-62. https://journals.sagepub.com/doi/full/10.1016/s1535-5535-04-00183-2.

International Search Report and Written Opinion of corresponding International Application No. PCT/CA2019/051846 dated Feb. 28, 2020, 9 pages.

Corrected International Search Report and Written Opinion of corresponding International Application No. PCT/CA2019/050859 dated Oct. 1, 2019, 9 pages.

* cited by examiner

A)
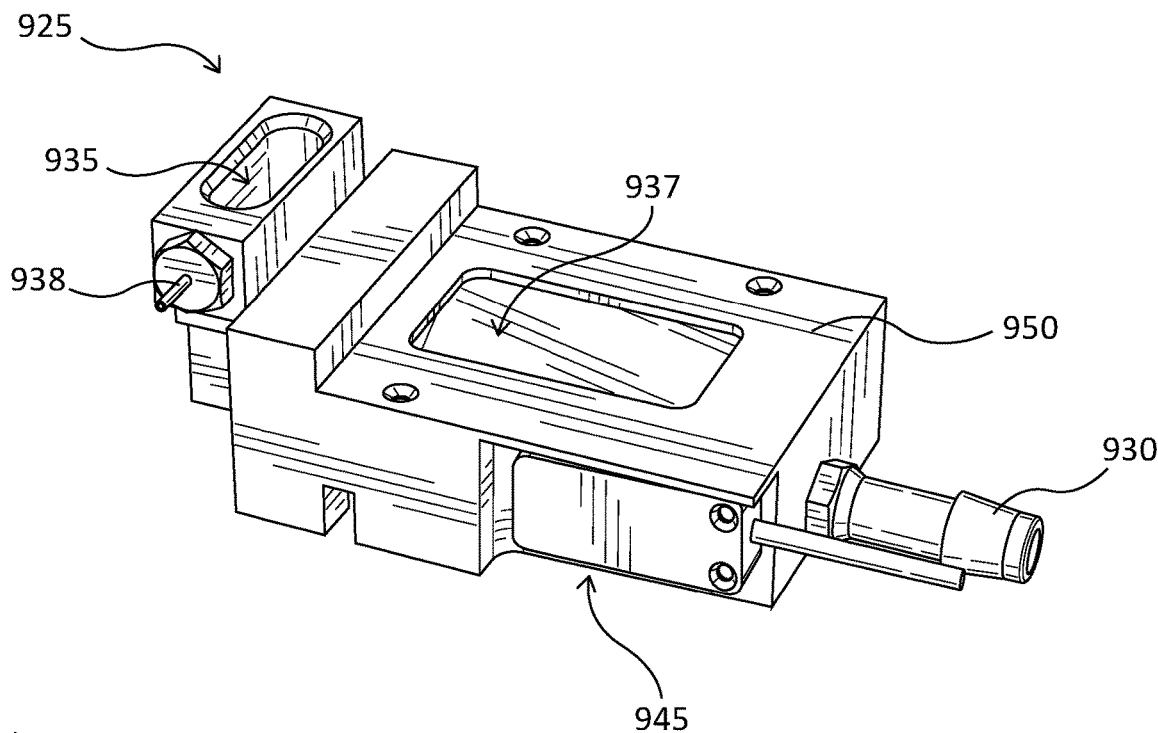
B)
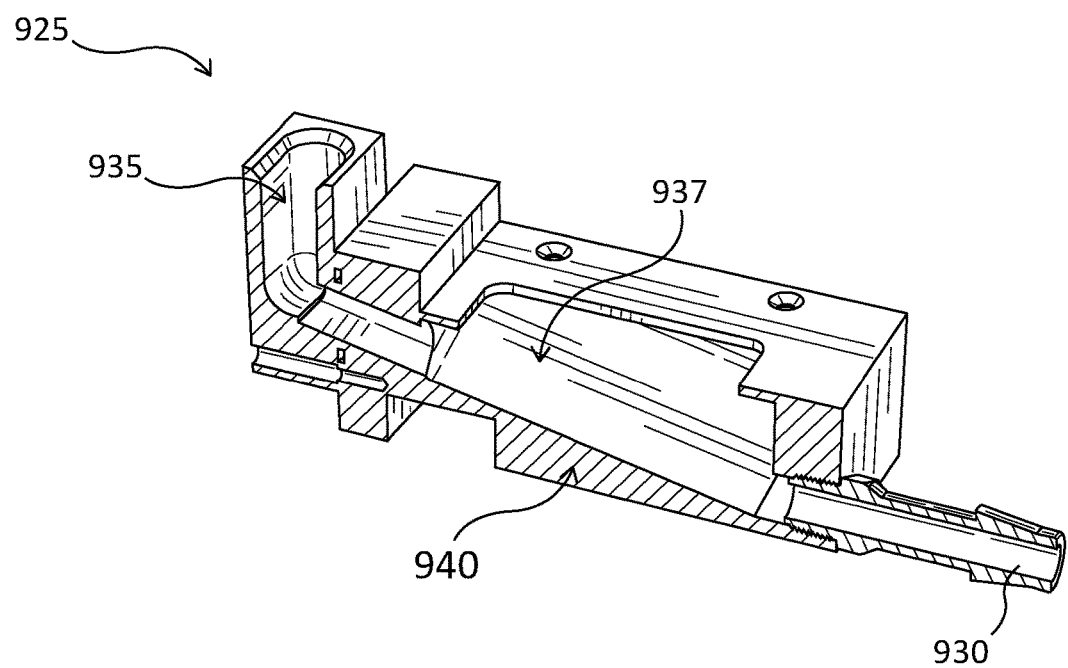
Figure 14

SYSTEMS, METHODS AND APPARATUS FOR THE AUTOMATED CULTURE OF CELLS

CROSS-REFERENCE TO RELATED APPLICATION

This application claims priority to U.S. Provisional Patent Application No. 62/686,962 filed on Jun. 19, 2018, the entire contents of which are hereby incorporated herein by reference.

FIELD

This disclosure relates to the culture of cells, and more particularly to the automated culture of cells.

BACKGROUND

Among other things, the maintenance of cultures of cells may involve frequent changes of culture media, monitoring of cell density, passaging or subculturing for the purpose of downstream applications, such as maintenance or expansion, and harvesting of cultured cells for downstream applications.

Depending on the scale of cell culture in a laboratory, the day-to-day maintenance of cells may be unduly burdensome on a researcher's or technician's time. In addition, inconsistency in cell culture practices, whether on the part of a single researcher or technician or among members of a team, may lead to suboptimal cell characteristics, such as but not limited to viability, growth rate, phenotype, metabolism, or otherwise. Further, regular cell culture may lead to repetitive strain disorders among involved researchers or technicians.

In instances where the scale of cell culture in a laboratory is not necessarily large, the downstream applications of the cultured cells may also dictate certain cell culture practices. For example, if cultured cells will be used in clinical applications, a certain level of regulatory compliance may be required that minimizes human contact with the cell culture. Alternatively, regulations or guidelines may require the consistent culturing/sub-culturing of cell cultures in both space and time.

Indeed, the automated culture of cells may address some of the foregoing concerns while potentially providing other benefits too.

One aspect of automated approaches to the culture of cells, including but not limited to stem cells, that remains unaddressed by the prior art relates to the consistent culturing/subculturing from one passage to another. A different or related challenge of culturing/subculturing cells may arise from the different growth dynamics of cells either in different wells of a cell culture vessel or different cell culture vessels. These and other challenges are exacerbated when culturing sensitive cell types such as primary cells or stem cells. Specific examples of sensitive stem cells may include mesenchymal stem cells (MSC), epithelial stem cells, neural stem cells, embryonic stem cells (ESC) and induced pluripotent stem cells (iPSC). ESC and iPSC, among other pluripotent cell types, may be broadly referred to as pluripotent stem cells (PSC).

PSC tend to grow as dense adhered colonies or aggregates of up to thousands of cells. Upon certain visible, morphological or phenotypic cues, a researcher or technician will want to subculture the cells of a PSC culture. Indeed, mouse PSC may be subcultured after having been dissociated completely to single PSC or as clumps with little or no impact on forming new colonies in subsequent cultures. In contrast, human PSC tend to perform poorly in subsequent cultures when completely dissociated to single PSC due to, for example, karyotype instability. Rather, human PSC tend to perform better when dissociated into clumps of a small number (about 5 or more) of PSC ahead of subculture.

It is well known that culture conditions, such as at the time of passaging, influence the properties of a culture of cells and thus effect their utility in downstream applications. The foregoing underlines the importance of consistent cell culture practices in order to have confidence in the reproducibility of results in downstream applications. Therefore, it is important to passage a culture of cells at the optimal time point and not at the most convenient time point for a researcher or technician. In view of the intricacies of culturing/subculturing cells, including but not limited to stem cells such as PSC, several of which have been described in the foregoing, there is a need for an automated cell culture system that can adaptively culture and passage cells with a view to obtaining consistent cultures of progeny in subsequent passages.

SUMMARY

The disclosure describes systems and methods for culturing a culture of cells. In a particular embodiment, the culture of cells may be pluripotent stem cells, and optionally may be human pluripotent stem cells. In a more particular embodiment, the culture of cells, such as human pluripotent stem cells, may be cultured as adhered cultures of cells. This disclosure also describes systems and methods for passaging or expanding a culture of cells, such as pluripotent stem cells. In some embodiments, the systems and methods are automated.

In one broad aspect, an automated system for adaptively passaging a culture of cells in a cell culture medium within a cell culture vessel is described herein. The automated system includes an imaging module for capturing one or more images of the culture of cells at a first time point and at one or more subsequent time points, a pipette module having one or more pipettes for drawing a fluid from the cell culture vessel through a pipette tip mateable with an end of the one or more pipettes, a liquid dispenser module spaced apart from the pipette module, the liquid dispenser module in fluid communication with more than one solution reservoir, a handling module having a pair of opposable arms for gripping and transporting the cell culture vessel or a lid thereof or a daughter cell culture vessel or a lid thereof within the automated system, and at least one processor in communication with the imaging module, the pipette module, the liquid dispenser and the handling module. The processor is configured to receive the one or more images from the imaging module, based on the one or more images received from the imaging module, calculate one or more characteristics of the culture of cells and execute an automated passaging protocol to passage the culture of cells, the protocol including coordinating operation of the pipette module, the liquid dispenser module and the imaging module based on comparing the calculated one or more characteristics of the culture of cells to: a learned threshold level for the one or more characteristics; or an inputted threshold level for the one or more characteristics.

In some embodiments, the one or more characteristics includes: a measure of a confluence of the culture of cells; a measure of a morphology of cells or colonies of the culture of cells; a measure of differentiation of cells or colonies of the culture of cells; a measure of colony size distribution of the culture of cells; a measure of the change of a), b), c), or d) from the first time point to the one or more subsequent time points; or a measure of a) relative to b), c) or d), a measure of b) relative to a), c), or d), a measure of c) relative to a), b), or d), or a measure of d) relative a), b), or c).

In some embodiments, the learned or the inputted threshold level is: for a), between about 30-90% for cell or colony confluence; for b), between about ±30% of a control culture; for c), between about 0 to 30% of a control culture in a maintenance protocol or between about 50% to 100% of a control culture in a differentiation protocol; or for d), within about 15% of a mean colony size distribution of a control culture, or a subfraction thereof.

In some embodiments, the one or more characteristics calculated in respect of the culture of cells in the cell culture vessel and the second culture of cells in a second cell culture vessel is different at the first time point or at the one or more subsequent time points and the one or more characteristics become more consistent during a subsequent passage.

In some embodiments, the imaging module includes a camera capable of resolving a single cell in the culture vessel.

In some embodiments, the system further includes a stage module for supporting the cell culture vessel.

In some embodiments, the stage module is movable in a first plane along a first axis or a second axis, or both.

In some embodiments, the stage module or a subcomponent thereof pivots about an edge thereof along a third axis.

In some embodiments, the one or more pipettes are attached to a carriage.

In some embodiments, the liquid dispensing module includes more than one conduits and each conduit is in fluid communication with a separate one of the more than one solution reservoirs.

In some embodiments, the liquid dispensing module includes a first conduit in fluid communication with a reservoir of a first solution and a second conduit in fluid communication with a reservoir of a second solution, and the first solution and the second solution are simultaneously dispensed into a daughter cell culture vessel.

In some embodiments, each conduit is reusable or replaceable.

In some embodiments, the system further includes an enclosure to house at least the imaging module, pipette module, liquid dispenser module, stage module, and handling module.

In some embodiments, the enclosure is sterile.

In some embodiments, the system further includes a refrigeration module to store one or more of the more than one solution reservoirs and a water reservoir, wherein the more than one solution reservoirs, the refrigeration module and the waste reservoir are external of the enclosure.

In some embodiments, the waste reservoir is in fluid communication with a waste trough within the enclosure.

In some embodiments, the waste trough is coated with a hydrophobic coating.

In some embodiments, the system further includes one or more sensors, wherein the one or more sensors are configured to detect and report on a mass of a load on the imaging module, on the stage module, or in the more than one solution reservoirs to: detect a mass of a load on the imaging module, on the stage module, or in the more than one solution reservoirs; and trigger an alert when the mass of the load is different than expected.

In some embodiments, the system further includes a closed conveyor module connecting the enclosure and an incubator module and for transporting the cell culture vessel from the incubator module into proximity of the handling module.

In some embodiments, the incubator module maintains permissive environmental conditions for the culture of cells.

In some embodiments, the system further includes a graphical user interface.

In some embodiments, the graphical user interface displays a fluid level report for each of the more than one solution reservoirs.

In another broad aspect, an automated system for adaptively passaging an adhered culture of pluripotent stem cells in a cell culture medium within a cell culture vessel is described herein. The automated system includes an imaging module for capturing one or more images of the culture of cells at a first time point and at one or more subsequent time points, a pipette module having one or more pipettes for drawing a fluid from the cell culture vessel through a pipette tip mateable with an end of the one or more pipettes, a liquid dispenser module spaced apart from the pipette module, the liquid dispenser module in fluid communication with more than one solution reservoir, a handling module having a pair of opposable arms for gripping and transporting the cell culture vessel or a lid thereof or a daughter cell culture vessel or a lid thereof within the automated system, and at least one processor in communication with the imaging module, the pipette module, the liquid dispenser and the handling module. The processor is configured to receive the one or more images from the imaging module, based on the one or more images received from the imaging module, calculate one or more characteristics of the culture of cells and execute an automated passaging protocol to passage the culture of cells, the protocol including coordinating operation of the pipette module, the liquid dispenser module and the imaging module based on comparing the calculated one or more characteristics of the culture of cells to: a learned threshold level for the one or more characteristics; or an inputted threshold level for the one or more characteristics.

In another broad aspect, an automated method for adaptively passaging a culture of cells is described herein. The method includes: providing the culture of cells in a cell culture medium within a cell culture vessel; capturing by an imaging module one or more images of the culture of cells at a first time point and at one or more subsequent time points; calculating by at least one processor communicatively coupled to the imaging module one or more characteristics of the culture of cells based on the one or more images; and executing by the at least one processor an automated passaging protocol based on comparing the calculated one or more characteristics of the culture of cells to: a learned threshold level for the one or more characteristics; or a pre-determined threshold level for the one or more characteristics.

In some embodiments, providing the culture of cells comprises conveying the culture of cells from an incubator.

In some embodiments, the method further includes positioning the cell culture vessel on a stage module.

In some embodiments, the method further includes obtaining a suspension of cells from the culture of cells and seeding some or all of the suspension of cells in a daughter cell culture vessel.

In some embodiments, prior to seeding in the daughter cell culture vessel the suspension of cells is passed through a first pipette tip to dissociate the culture of cells into a single cell suspension or a plurality of clumps having an average diameter not exceeding a bore diameter of the first pipette tip.

In some embodiments, obtaining the suspension of cells includes aspirating the cell culture medium from the cell culture vessel and contacting the culture of cells in the cell culture vessel with a detachment solution.

In some embodiments, the detachment solution is a fractionation solution, and the fractionation solution selectively detaches either a first population of differentiated cells or a second population of undifferentiated cells from a wall of the cell culture vessel.

In some embodiments, the method further includes dispensing a first solution and a second solution simultaneously into the daughter cell culture vessel prior to seeding the suspension of cells.

In some embodiments, the first solution is the cell culture medium and the second solution is a solubilized extracellular matrix.

In some embodiments, the culture of cells are pluripotent stem cells.

In some embodiments, the pluripotent stem cells are human pluripotent stem cells.

In some embodiments, the pluripotent stem cells are passaged as clumps.

In another broad aspect, an automated method for adaptively passaging an adhered culture of pluripotent cells is described herein. The method includes: providing the culture of cells in a cell culture medium within a cell culture vessel; capturing by an imaging module one or more images of the culture of cells at a first time point and at one or more subsequent time points; calculating by at least one processor communicatively coupled to the imaging module one or more characteristics of the culture of cells based on the one or more images; and executing by the at least one processor an automated passaging protocol based on comparing the calculated one or more characteristics of the culture of cells to: a learned threshold level for the one or more characteristics; or a pre-determined threshold level for the one or more characteristics.

In some embodiments, the method also includes aspirating the cell culture medium from the cell culture vessel and contacting the adhered culture of pluripotent stem cells in the cell culture vessel with a detachment solution to yield a suspension of cells.

In some embodiments, the detachment solution is a fractionation solution yielding the suspension of cells as either a selectively detached first population of differentiated cells or a second population of undifferentiated cells from a wall of the cell culture vessel.

In some embodiments, the suspension of cells includes clumps of pluripotent stem cells having an average diameter not exceeding a bore diameter of a first pipette tip through which the suspension of cells is passed.

In some embodiments, the method also includes seeding the suspension of cells into a daughter culture vessel.

In some embodiments, the method also includes dispensing a first solution and a second solution simultaneously into the daughter culture vessel prior to seeding the suspension of cells.

In some embodiments, the first solution is the cell culture medium and the second solution is a solubilized extracellular matrix.

In another broad aspect, methods for dissociating one or more colonies in a culture of cells are provided. The methods include: providing an apparatus in accordance with this disclosure; positioning a cell culture vessel containing the one or more colonies of cultured cells having been exposed to a detaching solution on a platform of the apparatus; rotating the platform under the influence of the drive; and colliding repeatedly one or more impact brackets of the apparatus with the one or more impact bumpers of the apparatus, the one or more impact brackets coupled to the platform to transmit a force on the platform and the cell culture vessel thereon to dissociate the one or more colonies in the culture of cells.

In some embodiments, the methods may further comprise securing the culture of cells to the platform.

In some embodiments, rotating the platform may be in a clockwise direction. In some embodiments, rotating the platform may be in a counterclockwise direction.

In some embodiments, the methods may further comprise oscillating rotation of the drive between a clockwise and a counterclockwise direction. In specific embodiments, oscillating may include a delay of less than 5 seconds between rotating in the clockwise and counterclockwise direction. In more specific embodiments, oscillating may include a delay of less than 1 second between rotating in the clockwise and counterclockwise direction. In still more specific embodiments, oscillating may include a delay of about 0.5 milliseconds or less between rotating in the clockwise and counterclockwise direction.

In some embodiments, the one or more colonies of cultured cells may be directly or indirectly adhered to a well bottom of the cell culture vessel.

In some embodiments, the one or more colonies of cultured cells may be one or more undifferentiated colonies in a culture of pluripotent stem cells.

In another broad aspect, an automated system for passaging pluripotent stem cells is provided. The system includes: a stage module for supporting one or more cell culture vessels; a cell culture vessel handling module; a pipette module; a liquid dispenser module spaced apart from the pipette module, the liquid dispenser module in fluid communication with more than one solution reservoirs; a dissociation module according to the apparatus of any one of claims 1 to 14; a waste reservoir; and a controller for coordinating operation of each of the modules of the automated system.

In some embodiments, the stage module may include a platform, and the platform, or subcomponent thereof, may be movable. In some embodiments, the platform, or subcomponent thereof, may be movable in a first plane. In some embodiments, the platform, or subcomponent thereof, may be movable in a path along a first axis and a second axis. In some embodiments, the platform, or subcomponent thereof, may also move in a path along a third axis.

In some embodiments, the handling module may include a pair of opposable arms.

In some embodiments, the pipette module may include more than one pipette, and an end of each pipette is mateable with a disposable pipette tip.

In some embodiments, the pipette module and the handling module are both included in a movable unit.

In some embodiments, the liquid dispensing module may include more than one line and each line may be in fluid communication with a separate one of the more than one solution reservoirs. In some embodiments, each line of the more than one line may be reusable. In some embodiments, each line of the more than one line may be replaceable.

In some embodiments, the system may further include an imaging module, wherein the imaging module includes a camera capable of resolving a single cell in a well of the one or more culture vessels. In some embodiments, the imaging module may include an image processor to interrogate a characteristic of a culture of pluripotent stem cells in the well of the one or more culture vessels.

In some embodiments, the system may further include an incubator module, wherein the incubator module maintains permissive environmental conditions for the culture of pluripotent stem cells.

In some embodiments, the system may further include a conveyor module to transport the one or more cell culture vessels from the incubator into proximity of the handling module.

In some embodiments, the system may further include a refrigeration module to store one or more of the more than one solution reservoirs.

In some embodiments, the system may further include a housing for at least the stage module, handling module, pipette module, and the vortex module.

In some embodiments, the more than solution reservoirs, the refrigeration module, and the waste reservoir are external of the housing.

In some embodiments, the system may further include a graphical user interface. In some embodiments, the graphical user interface may display a fluid level report for each of the more than one solution reservoirs.

In another broad aspect, methods for automated passaging of cells are provided. The methods include: providing a system as disclosed herein; positioning a first cell culture vessel of cells on the stage module using the handling module; aspirating culture medium from a well of the first cell culture vessel using the pipette module; dispensing a dissociation solution into the well of the first cell culture vessel using the liquid dispensing module; detaching a cell colony from a bottom of the well of the first cell culture vessel using the dissociation module; dissociating the detached cell colony into a suspension of cells; and seeding a volume of the suspension of cells into a well of a second cell culture vessel using the pipette module.

In some embodiments, the methods may further include conveying from the incubator module the first cell culture vessel, prior to the positioning step, using the conveyor module.

In some embodiments, the methods may further include tilting the first cell culture vessel, prior to the aspirating step, using the stage module.

In some embodiments, the methods may further include washing the well of the first cell culture vessel, after the aspirating step, with a wash buffer dispensed using the liquid dispensing module.

In some embodiments, the methods may further include incubating, after the dispensing step, the first cell culture vessel in the incubator module.

In some embodiments, the methods may further include triturating the detached colony of cells into a suspension of cells.

In some embodiments, the methods may further include positioning a second cell culture vessel on the stage module, prior to the seeding step, using the handling module.

In some embodiments, the methods may further include conveying the second cell culture vessel to the incubator module using the conveyor module.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DESCRIPTION OF DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 14 shows a perspective view (A) and cross-section perspective view (B) of one embodiment of a waste trough used in an automated system described herein.

DETAILED DESCRIPTION

Figure 1:
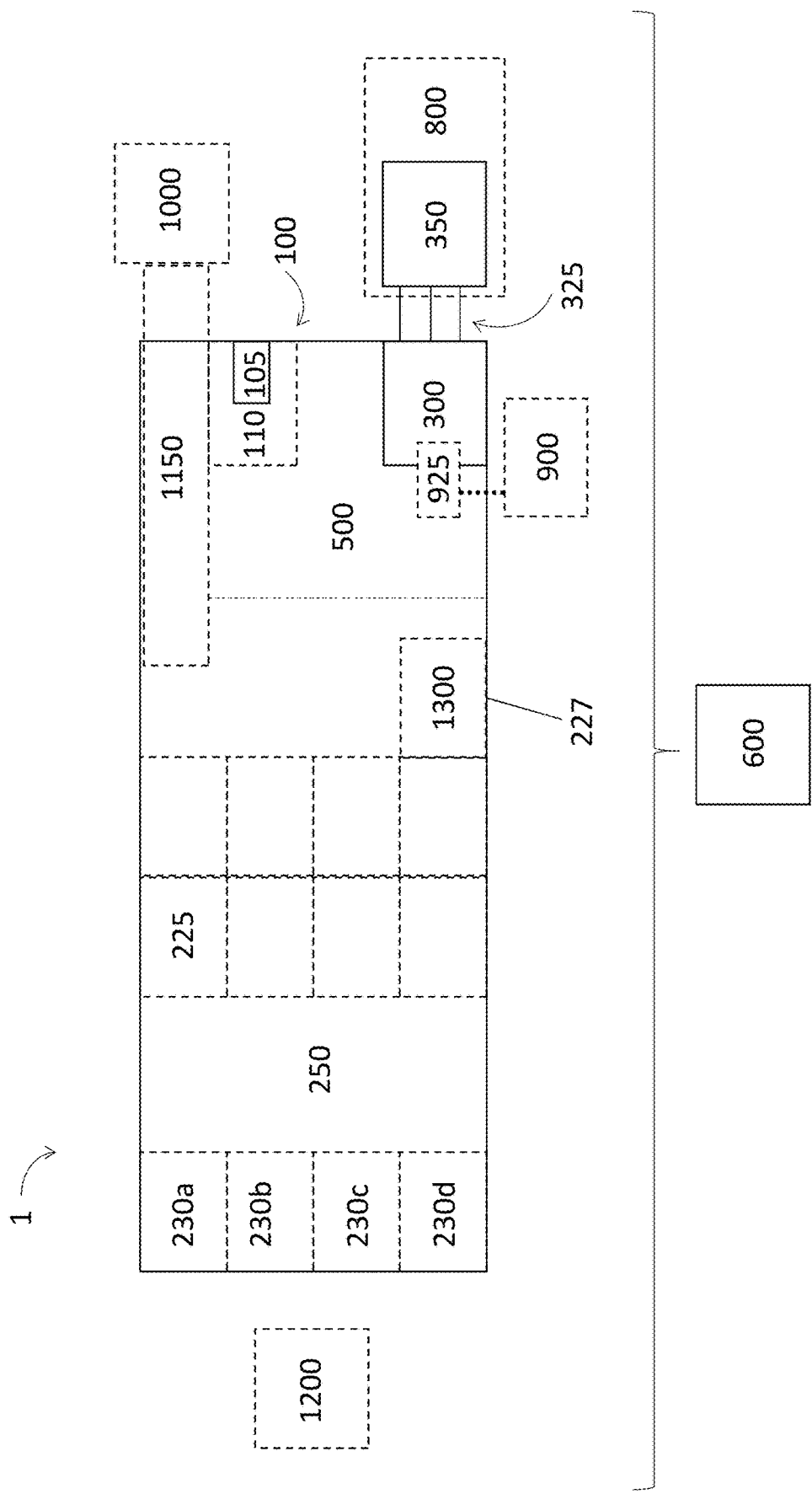
FIG. 1 shows a top plan view of one embodiment of an automated system for passaging a culture of cells. Optional elements are shown with dashed lines.

Various systems, apparatus and methods are described below to provide an example of at least one embodiment of the claimed subject matter. No embodiment described below limits any claimed subject matter and any claimed subject matter may cover systems, apparatus and methods that differ from those described below. The claimed subject matter are not limited to systems, apparatus and methods having all of the features of any one system, apparatus or method described below or to features common to multiple or all of the systems, apparatus and methods described below. Subject matter that may be claimed may reside in any combination or sub-combination of the elements or process steps disclosed in any part of this document including its claims and figures. Accordingly, it will be appreciated by a person skilled in the art that a system, apparatus or method disclosed in accordance with the teachings herein may embody any one or more of the features contained herein and that the features may be used in any particular combination or sub-combination that is physically feasible and realizable for its intended purpose.

Furthermore, it is possible that systems, apparatus or methods described below is not an embodiment of any claimed subject matter. Any subject matter that is disclosed in a system, apparatus or method described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

It will also be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The disclosure describes systems, apparatus and methods for culturing or dissociating one or more colonies in a culture of cells. In a particular embodiment, the culture of cells are pluripotent stem cells, and optionally are human pluripotent stem cells. In a more particular embodiment, the culture of cells, such as human pluripotent stem cells comprises dissociating the one or more colonies into clumps or clusters of human pluripotent stem cells. This disclosure also describes integrating the apparatus and/or methods into systems and methods for passaging or expanding a culture of cells. In a particular embodiment, the systems and methods are automated.

Where used herein, "passaging" refers to the cell culture activities up to a point in time when a culture of cells may be passaged or subcultured, and the activities related to passaging or subculturing a culture of cells, including seeding some or all of the culture of cells with fresh culture medium into one or more daughter cell culture vessels. Thus, the term passaging inclusively refers to the activities related to the routine culturing of cells, such as sub-culturing the culture of cells, and also to workflows aimed at expanding, harvesting (such as for cryopreservation), or differentiating a culture of cells, or onboarding a newly derived cell line. In one embodiment, a volume of a suspension of cells from a first cell culture vessel may be seeded in only one daughter cell culture vessel (i.e. 1:1 passaging). In one embodiment, a volume of a suspension of cells from a first cell culture vessel may be seeded into a plurality of daughter cell culture vessels (i.e. 1:n+1 passaging, which may be considered a form of expansion).

Where used herein, "culture of cells" refers to any type of cell that may be cultured, passaged, expanded, or differentiated in a cell culture vessel. In one embodiment, the cells are anchorage independent cells, such as hematopoietic stem cells or a progenitor thereof. In one embodiment, the cells are anchorage dependent cells, such as those that are cultured in a monolayer or as an adhered culture of cells. In one embodiment, the anchorage dependent cells are mesenchymal stem cells. In one embodiment, the anchorage dependent cells are pluripotent stem cells ("PSC"). The PSC may be embryonic stem cells, naïve stem cells, extended pluripotent stem cells, or induced pluripotent stem cells.

Where used herein, "cell culture vessel" or "daughter cell culture vessel" refers to a container that may be used to support a culture of cells. A cell culture vessel may be a single flask or dish, such as a circular dish, or may be a multiwell culture plate. Where the cell culture vessel corresponds to a multiwell culture plate—each well, some wells, or all the wells thereof—may be considered a cell culture vessel. Specifically, after carrying out a passaging method and upon seeding the culture of cells in a new cell culture vessel, such new cell culture vessel is referred to as a daughter cell culture vessel herein.

Systems

In one aspect of the disclosure, systems for passaging a culture of cells are described. In one embodiment, the cells are PSC, and even more specifically the cells may be human PSC. In one embodiment, the PSC, human or otherwise, are cultured or passaged as an adhered culture of cells. Since it is desirable in many applications to passage cells such as human PSC as clumps or clusters, the automated systems and methods for passaging such cells may be suited to the clump passaging thereof.

Figure 3:
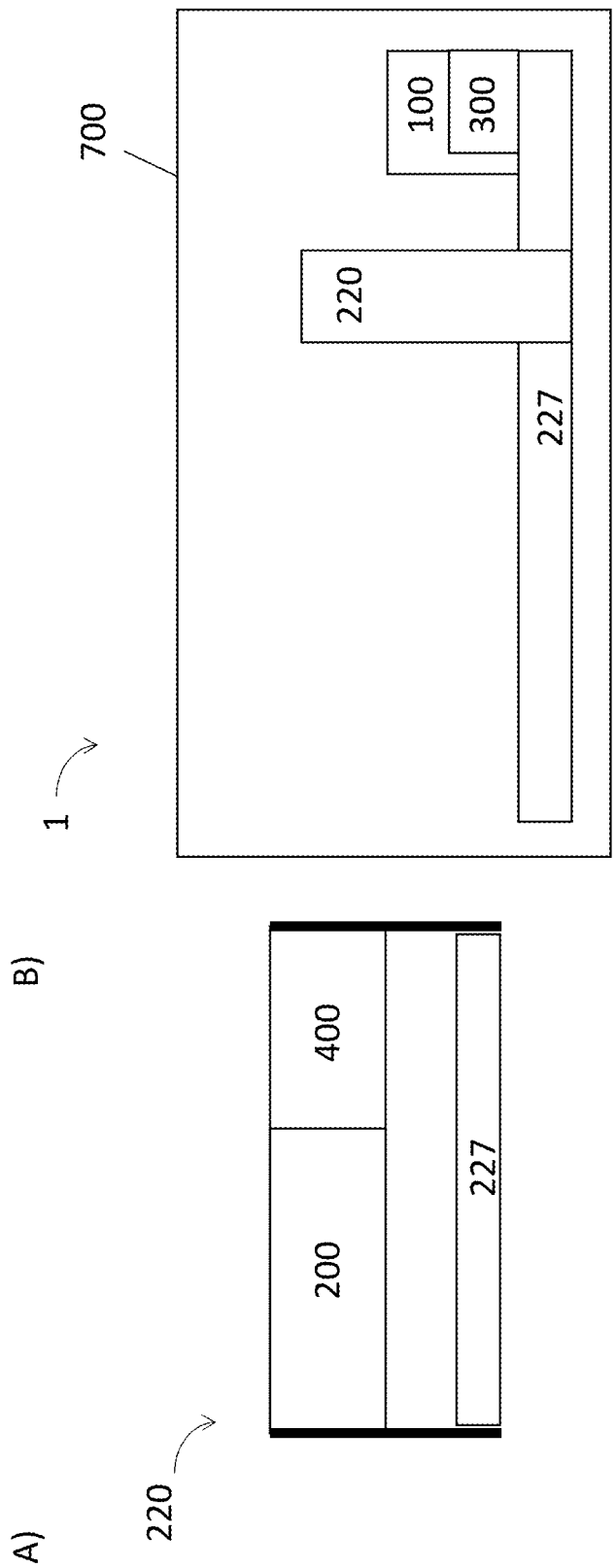
FIG. 3 shows a front view of one embodiment of a carriage as used in the automated system described herein (A) and a side view of one embodiment of the automated system described herein (B).

In one embodiment, an automated system 1 for passaging a culture of cells, such as human pluripotent stem cells, comprises a variety of modules, including: an imaging module 100; a pipette module 200; a liquid dispenser module 300; more than one solution reservoirs 350 (for example 350a, 350b, 350c, etc.); a handling module 400; optionally a stage module 500, and a processor 600 for coordinating operation of each of the modules of the automated system (see FIGS. 1 and 3).

Figure 2:
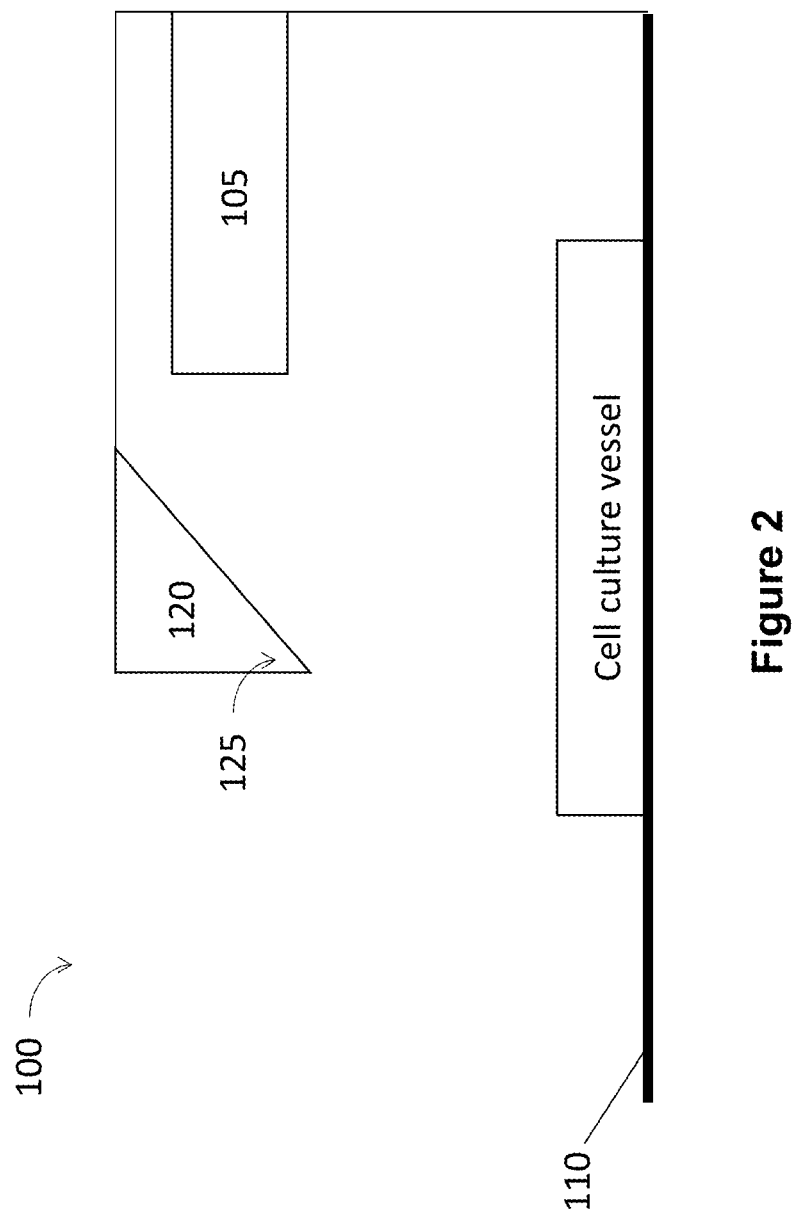
FIG. 2 shows a side view of one embodiment of an imaging module used in the automated system described herein.

Imaging module 100 includes a camera 105, which in one embodiment may be positioned above a stage 110 (FIG. 2). In one embodiment, camera 105 may be either fixed or movable above stage 110. In one embodiment, camera 105 may either be fixed or movable beneath stage 110. When a cell culture vessel is positioned on stage 110, camera 105 may capture one or more images at appropriate scale and resolution of the culture of cells in the cell culture vessel at a first time point and at one or more subsequent time points.

In one embodiment, a lens of camera 105 (not shown) is pointed in substantially a horizontal direction relative to a plane of stage 110, and the one or more images of the culture of cells are captured with reliance on a reflective mirror 120 (see FIG. 2). Mirror 120 is positioned an appropriate distance from the lens of camera 105 and is also sufficiently angled in order to reflect an object plane (i.e. the culture of cells within the cell culture vessel) to a focal plane of camera 105. In one embodiment, angle 125 of mirror 120 is about 45°.

Camera 105 is associated with sufficient computer readable memory to store the one or more images as may be captured for thousands of culture vessels over dozens of time points. The computer readable memory may be localized to camera 105 and/or the computer readable memory may be stored remotely such as in a personal computer device or on the cloud (i.e. on a remote server).

In one embodiment camera 105 captures moving or still images. In one embodiment camera 105 captures black and white (or greyscale) or colored still images. In one embodiment, the one or more images are captured using dark-field techniques, wherein the field around the culture of cells is generally dark while the culture of cells provides the sample contrast.

In one embodiment, camera 105 is capable of imaging an area of a cell culture vessel used to culture cells. In such an embodiment, the cell culture vessel may be a 35 mm dish or 100 mm dish. Also in such an embodiment, the cell culture vessel may be a 6-well plate and camera 105 may capture a single image that includes the cell culture area of each of the 6-wells thereof. Such an image may be stored as is, or, for example, it may be stored with six associated files as a subset corresponding to a cropped image of each well thereof. In one embodiment, six separate images may be captured corresponding to each well of the 6-well plate. The skilled person will appreciate that the cell culture vessel may be in any format, such as but not limited to a 12-, 24-, 96-, or 384-well plate, and in any case camera 105 may capture one or images that includes each of the wells thereof (or a desired subset) or individual images of each well thereof (or a desired subset).

In certain embodiments, camera 105 may be capable of resolving a single cell in the cell culture vessel, or in a well thereof. In such an embodiment or in a different embodiment, camera 105 is capable of resolving a single colony of a culture of cells in the cell culture vessel, or in a well thereof. Since camera 105 may be capable of capturing an image of an entire cell culture vessel (or a well thereof), camera 105 may also be capable of resolving each of the single cells or colonies of a culture of cells within a cell culture vessel.

In some embodiments, imaging module 100 includes an image processor to interrogate one or more characteristics of a culture of cells, such as PSC, in the cell culture vessels. Through interrogating the one or more characteristics, system 1 may execute an appropriate operation, such as a media change protocol, a passaging protocol, an expansion protocol, a differentiation protocol, or a culture termination protocol. In other embodiments a processor for interrogating the one or more characteristics is not included within imaging module 100, but may rather be included separately, such as within a centralized processor module as may be included within a computer device. Thus, system 1 may include at least one processor (described in more detail below).

In one embodiment, stage 110 includes one or more load cells to detect and report on the presence and weight of a cell culture vessel thereupon. The one or more load cells may thus provide feedback to system 1 on whether or not to commence an operation. For example, an absence of a cell culture vessel from stage 110 may signal that an imaging operation should not be executed. In one embodiment, the one or more load cells verify whether or not an appropriate volume of a solution has been added to or removed from a cell culture vessel. In one embodiment, the one or more load cells are sufficiently sensitive to verify whether or not a lid has been removed from a cell culture vessel.

In one embodiment, stage 110 is separate from stage module 500. In one embodiment, stage 110 is a subcomponent of stage module 500. In one embodiment, stage 110 and stage module 500 are one and the same.

System 1 also comprises a pipette module 200. Pipette module 200 includes one or more pipettes for drawing a fluid, such as a cell culture medium, from the cell culture vessel through a pipette tip mateable with an end of the one or more pipettes. Pipette module 200 also includes, in fluid communication with each of the one or more pipettes, a means of generating the necessary suction to draw the fluid from the cell culture vessel.

In one embodiment, the one or more pipettes of pipette module 200 may be lowered or raised to bring a pipette tip attached thereto into or out of contact with a fluid in a cell culture vessel. In one embodiment, the cell culture vessel may be raised or lowered to bring a pipette tip of the one or more pipettes into or out of contact with a fluid therein.

Whether or not the one or more pipettes may be raised or lowered in the vertical plane, it may also be desirable that pipette module 200 and the one or more pipettes thereof move within system 1 along either or both the x or y axes relative to a horizontal plane of stage 110. In such an embodiment, the pipette module 200 may be comprised in a movable unit 220 (or carriage), for example by attachment of the pipette module 200 thereto (FIG. 3). In one embodiment, carriage 220 may move along tracking within system 1, which tracking may be suspended above or rooted to a deck 227 of system 1. In one embodiment, carriage 220 may run along the length or substantially along the length of one or both sides of the deck. Such carriages are known in the art, and an exemplary carriage includes the Nimbus' (Hamilton Company) system.

In one embodiment, the pipette tip is disposable, thus the one or more pipettes may also comprise a pipette discharging mechanism. One example of a pipette discharging mechanism comprises a collar that slides over a tubular body of the one or more pipettes, and disengages the pipette tip from the tubular body when an edge of the collar contacts the pipette tip.

Exemplary instances of the use of pipette module 200 may include but are not limited to: triturating a suspension of cells; aspirating fluid from a cell culture vessel for waste; or transferring some or all of the fluid of a cell culture vessel to a daughter cell culture vessel, such as when a daughter cell culture vessel is seeded with cells during an automated passaging protocol.

System 1 may also include staging areas for a plurality of racks of pipette tips. System 1 may accommodate more than one in-use rack of tips, and may accommodate more than one back-up tip racks. In one embodiment, pipette tip rack 225 may correspond to an in-use rack of pipette tips, while pipette tip racks 230*a*, 230*b*, 230*c*, and 230*d* may correspond to back-up tip racks. Upon exhausting the pipette tips within pipette tip rack 225 a consumed tip rack may be substituted with a back-up tip rack (230*a*, 230*b*, 230*c*, or 230*d*). When all pipette tips within system 1 are consumed, a user of system 1 may reload the staging areas with fresh racks of pipette tips. The staging areas (boxes in series with pipette tip rack 225) may also be used for storing cell culture vessels or lids thereof that should be accessible but are not currently positioned in proximity to either stage 110, stage module 500.

In order to minimize the chances of unnecessarily contaminating system 1 or any component thereof, the region of system 1 where pipette tips are disengaged from an end of the one or more pipettes is an important consideration. Specifically, such region should be remote from any component of system 1 coming into contact with a cell culture vessel, the pipette tip rack staging area(s), and the in-use rack of pipette tips. In one embodiment, pipette tips are disengaged from the one or more pipettes into a waste receptacle 250. In one embodiment, waste receptacle 250 may be comprised in a slidable drawer in order to facilitate removal of the contents thereof from system 1 while also minimizing user contact with components of system 1 such as imaging module 100, pipette module 200, pipette tip racks 225 and 230, and the other modules described below. In one embodiment, a sensor detects and reports on the positioning of waste receptacle 250, so as not to impede the movement of carriage 220, for example.

System 1 further comprises a liquid dispensing module 300. Liquid dispensing module 300 may be spaced apart from pipette module 200. For clarity, spaced apart means these are distinct elements of system 1, and possibly in different locations of system 1. Whereas liquid dispensing module 300 is used to dispense a solution in bulk into a cell culture vessel, pipette module 200 is used to draw some or all of a fluid from a cell culture vessel. Exemplary instances of the use of liquid dispensing module 300 may include dispensing: a cell culture or differentiation medium into a cell culture vessel or a daughter cell culture vessel either before or after it has been seeded with a suspension of cells; a wash buffer or a cell detachment solution to a cell culture vessel during an automated passaging protocol of a culture of cells within a cell culture vessel; or a cell culture matrix solution (e.g. a solubilized extracellular matrix).

Liquid dispensing module 300 includes more than one conduit 325 in fluid communication with more than one solution reservoir 350 (for example see FIG. 1). Solution reservoirs 350 contain various solutions for carrying out the automated culture or passaging of cells, such as pluripotent stem cells. Examples of solutions that may be contained in solution reservoirs 350 include but are not limited to a cell culture medium, a cell differentiation medium, a cell culture matrix solution (e.g. a solubilized extracellular matrix), a cell washing buffer, and a cell detachment solution or a cell dissociation solution.

The contents of solution reservoirs 350 may depend on the workflows adopted by users of system 1, and may be exchanged as required by the user. Non-limiting examples of workflows may include feeding cells, passaging cells, expanding cells, onboarding cells, deriving clonal populations of cells, or differentiating cells. Such workflows are particularly common among users interested in automating aspects of pluripotent stem cell cultures.

Solution reservoirs 350 may hold any reasonable volume of the solutions used in the workflows adopted by users of system 1. For example, solution reservoirs 350 may correspond to 500 mL bottles commonly used to contain cell culture solutions. Alternatively, solution reservoirs 350 may correspond to larger bottles or bags, such as one gallon or 10 L carboys. In some embodiments, solution reservoirs 350 may hold different volumes of solutions. For example, solutions that are used in greater volumes may be provided in relatively larger reservoirs, while solutions that are used in smaller volumes may be provided in relatively smaller reservoirs.

As mentioned, solution reservoirs 350 are in fluid communication with more than one conduit 325 of liquid dispensing module 300. The more than one conduit may take on any form provided it is capable of transmitting a solution therethrough. In one embodiment, each of the more than one conduits corresponds to flexible tubing. In order to transmit a solution through each of the more than conduits, solution reservoirs 350 and the more than one conduit may be associated with a pump. In one embodiment, the pump is a peristaltic pump. In one embodiment, the pump may operate analogously to a sump pump pulling a solution through a conduit from a solution reservoir.

Liquid dispensing module 300 may include more than one conduit and each conduit may be in fluid communication with a separate one of the more than one solution reservoirs 350, for example first conduit 325*a* in fluid communication with first reservoir 350*a*, and so on (not shown). In embodiments where liquid dispensing module 300 includes more than one conduit and each conduit is in fluid communication with a separate one of the more than solution reservoirs 350, each conduit may be reusable and/or replaceable.

In one embodiment, liquid dispensing module 300 may include a first conduit in fluid communication with a reservoir of a first solution and second conduit in fluid communication with a reservoir of a second solution, and the first solution and the second solution are dispensed at different times. For example, the first solution may be a wash buffer and the second solution may be a cell detachment solution or a cell dissociation solution. Accordingly, an appropriate volume of the first solution may be dispensed into a cell culture vessel (which may or may not include a culture of cells), and after removing the first solution, such as by using pipette module 200, an appropriate volume of the second solution may be dispensed into the cell culture vessel. Alternatively, the first solution may correspond to the cell detachment solution or the cell dissociation solution and the second solution may correspond to a cell culture medium. Alternatively, the first solution may correspond to a cell culture matrix and the second solution may correspond to a cell culture medium.

In one embodiment, liquid dispensing module 300 may include a first conduit in fluid communication with a reservoir of a first solution and second conduit in fluid communication with a reservoir of a second solution, and the first solution and the second solution are simultaneously dispensed. For example, the first solution may be a cell culture matrix solution and the second solution may be a cell culture medium. Accordingly, an appropriate volume of the first solution may be dispensed into a cell culture vessel (which may or may not include a culture of cells) and without removing the first solution an appropriate volume of the second solution may also be dispensed into the cell culture vessel.

System 1 further comprises a cell culture vessel handling module 400 (see FIG. 3). Handling module 400 may comprise a pair of opposable arms for grasping and transporting cell culture vessels or the lids thereof, or a daughter cell culture vessel or a lid thereof, within automated system 1. Handling module 400 having grasped a cell culture vessel or a lid thereof may transport the vessel or the lid to a different station (i.e. module) of system 1.

Handling module 400 may also shuttle pipette tip racks within system 1. In one embodiment, handling module 400 may transport a pipette tip rack consumed of pipette tips from the in-use location to either the waste receptacle 250 or to a staging area for consumed pipette tip racks. Handling module 400 may then transport a back-up rack of pipette tips 230 to the in-use location. In an alternative embodiment, a user may shuttle pipette tip racks within system 1.

Handling module 400 may also be comprised in carriage 220 along with pipette module 200 (FIG. 3A). In one embodiment, handling module 400 is an element distinct from pipette module 200 of carriage 220. In one embodiment, pipette module 200 may also perform functions of handling module 400. For example, a pair of paddles may be mated to the ends of two pipettes (instead of pipette tips), and the pair of paddles may be used to grasp and transport a cell culture vessel or a lid thereof within system 1. In one embodiment, handling module 400 and pipette module 200 may both be comprised as distinct elements of carriage 220, and pipette module 200 may also provide the gripping functionality via mating the ends of two pipettes thereof with the pair of paddles.

System 1 may further comprise a stage module 500 for supporting one or more cell culture vessels positioned thereupon. Stage module 500 may at least partially underlie liquid dispenser module 300 and may also at least partially underlie imaging module 100 (FIG. 1).

Stage module 500 may include a platform 510, wherein stage module 500 or platform 510, or a subcomponent thereof, is movable. Stage module 500 or platform 510, or the subcomponent thereof, may be movable in a first horizontal plane. In embodiments where stage module 500 or platform 510, or the subcomponent thereof, is moveable in the first horizontal plane, it may be movable in a path along a first axis (i.e. an x axis) or in a path along a second axis (i.e. a y axis), or both.

Horizontal planar movement of stage module 500 or platform 510, or the subcomponent thereof may help to distribute the cells contained in a cell culture vessel, or in one or more wells thereof, such as upon seeding a volume of a suspension of cells therein. Horizontal planar movement may also help to distribute within a cell culture vessel, or within one or more wells thereof, a solution dispensed therein, such as a cell culture medium, a wash buffer, a detachment or dissociation solution, or a cell culture matrix solution (e.g. a solubilized extracellular matrix).

In one embodiment, stage module 500 or platform 510, or the subcomponent thereof, may also move in a path along a third axis. For example, stage module 500 or platform 510, or the subcomponent thereof may tilt or pivot vertically about an edge of stage module 500 or platform 510, or subcomponent thereof. In a specific embodiment, tilting occurs about an edge of the subcomponent of stage module 500, such as platform 510.

Tilting movement of stage module 500 or platform 510, or subcomponent thereof, may help to collect any solution that may be contained in the cell culture vessel into a corner thereof, including in each corner of the one or more wells thereof. Such collection of a solution within a cell culture vessel may facilitate triturating or aspirating operations of pipette module 200, including drawing a volume of a suspension of cells from a cell culture vessel for seeding in a daughter cell culture vessel. Thus, stage module 500 or platform 510, or subcomponent thereof, particularly where a cell culture vessel may be positioned thereon, should be accessible by the more than one pipettes of pipette module 200.

A particular function of handling module 400 may be to position a cell culture vessel on stage module 500 (or stage 110) prior to system 1 carrying out its various functions, such as capturing one or images, and prior to carrying out various steps of the methods of automated cell culture.

In one embodiment, stage module 500 includes one or more load cells to detect and report on the presence and weight of a cell culture vessel thereupon. The one or more load cells may thus provide feedback to system 1 on whether or not to commence an operation. For example, an absence of a cell culture vessel from stage module 500 may signal that a liquid dispensing operation should not be executed, thereby preventing unnecessary spillage and preventing system 1 form having to be taken off-line. In one embodiment, the one or more load cells are sufficiently sensitive to verify whether or not a lid has been removed from a cell culture vessel. In one embodiment, the one or more load cells are sufficiently sensitive to verify that liquid transfers of as little as about 100 μL have occurred.

In one embodiment stage 110 is comprised in stage module 500. In one embodiment, stage 110 is distinct from stage module 500.

System 1 further comprises at least one processor 600 communicatively coupled to at least imaging module 100, pipette module 200, liquid dispenser module 300, and handling module 400. In one embodiment, at least one processor 600 is communicatively coupled to at least imaging module 100, pipette module 200, liquid dispenser module 300, handling module 400, and stage module 500.

In respect of imaging module 100, at least one processor 600 may initiate commands whether or not to: position a cell culture vessel on stage 110 (or stage module module 500 or platform 510, or subcomponent thereof) or remove a cell culture vessel from stage 110 (or stage module module 500 or platform 510, or subcomponent thereof); capture one or more images; or calculate the one or more characteristics based on the one or more images.

In respect of pipette module 200, at least one processor 600 may initiate commands whether or not to: move from a first position in system 1 to a second position in system 1; aspirate a volume from a cell culture vessel, such as a volume of a suspension of cells; triturate (i.e. pipette up and down) a volume in a cell culture vessel; seed a volume of a suspension of cells in a daughter cell culture vessel; disengage a pipette tip from an end of the one or more pipettes; or discharge an aspirated volume into waste trough (see below).

In respect of liquid dispensing module 300, at least one processor 600 may initiate commands whether or not to: dispense a volume of liquid into a cell culture vessel; or specify which solution(s) are to be dispensed and what volume of such solution(s).

In respect of handling module 400, at least one processor 600 may initiate commands whether or not to: move from a first position in system 1 to a second position in system 1; move a cell culture vessel or a lid thereof from a first position in system 1 to a second position in system 1; remove a lid of a cell culture vessel; or move a pipette tip rack. At least one processor 600 may also initiate commands whether or not to engage the pair of paddles in preference to the pair of opposable arms of handling module 400.

In respect of stage module 500, at least one processor 600 may initiate commands whether or not to: move stage module 500 or platform 510, or subcomponent thereof in a path along the X-axis or Y-axis, or both; or tilt stage module 500 or platform 510, or subcomponent thereof along an edge thereof.

In one embodiment, system 1 comprises one central processor 600 for coordinating the operation of various modules of system 1 to execute an automated passaging, culturing, expansion or differentiation protocol. It should be noted that, where the term "passaging" is used below or anywhere herein, it is the intention that the terms culturing, expanding, or differentiating, or variations thereof, may be equally applicable. In such an embodiment, the processor 600 may be comprised in a computer device communicatively coupled to system 1.

In one embodiment, system 1 comprises more than one processor 600 for coordinating the operation of various modules of system 1 to execute an automated passaging, culturing, expansion or differentiation protocol. In such an embodiment, a first processor may be comprised in a first computer device communicatively coupled to system 1 and a second processor may be comprised in a second computer device, which may be integrated in a module of system 1 (such as the image processor of imaging module 100), and communicatively coupled to the first processor and system 1.

Nevertheless, at least one processor 600 is configured to receive one or images from imaging module 100 and, based on the one or more images received from imaging module 100, calculate one or more characteristics of the culture of cells.

In one embodiment, the one or more characteristics correspond to a measure of the confluence of a culture of cells within a cell culture vessel. The confluence of the culture of cells may be calculated by analyzing the one or more images to determine the surface area of the cell culture vessel covered by the culture of cells, or such other portion of the surface area used to make the determination, and dividing this value by the total surface area of the cell culture vessel, or the such other portion of the surface area used to make the determination. In one embodiment, a software script may be executed to transform each of the one or more images into a representation wherein a grey or greyscale pixilation is assigned to the culture of cells to contrast the culture of cells from a white background. In one embodiment, cells may be assigned a white, grey, or greyscale pixilation against a black background. Regardless, a transformed representation may be readily analyzed by at least one processor 600 of system 1 to determine the measure of the confluence of a culture of cells within the cell culture vessel.

Figure 4:
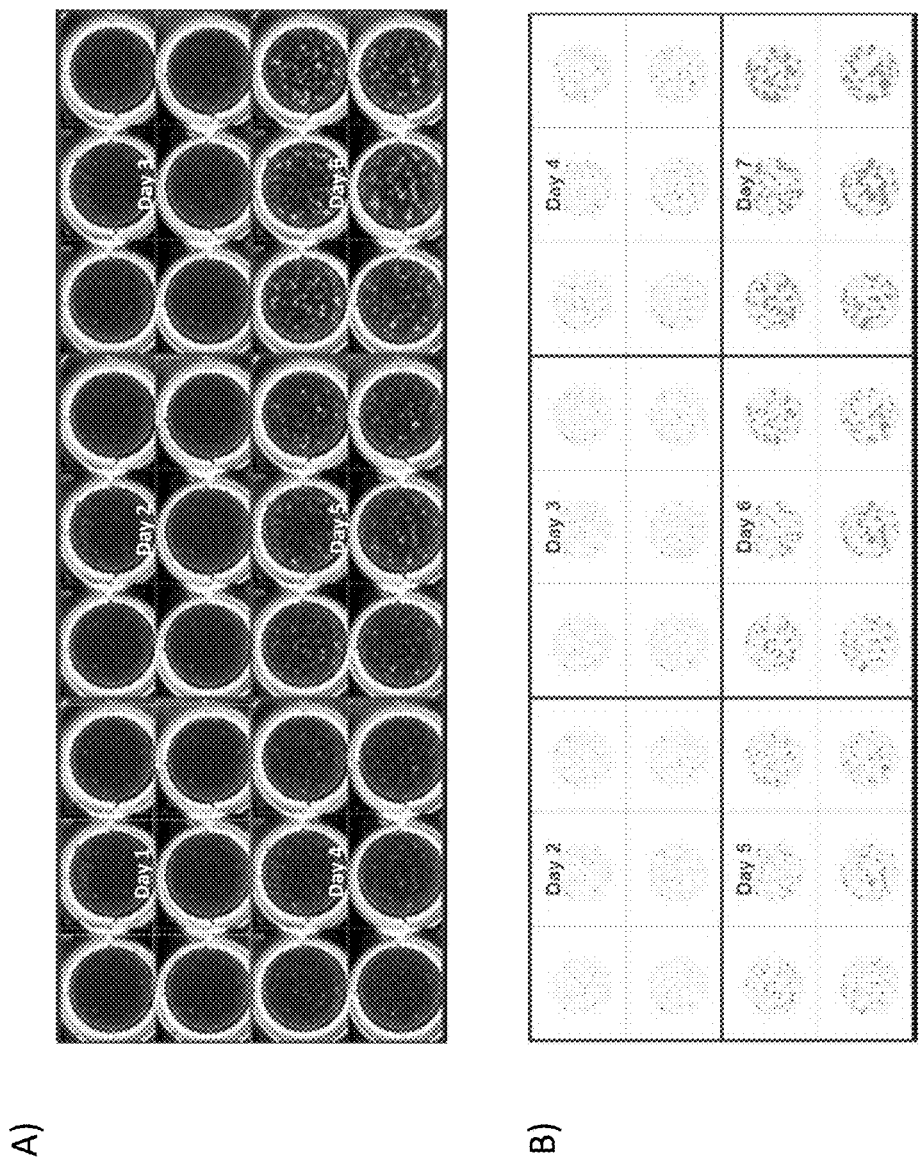
FIG. 4 shows representative images captured using the imaging module at different time points of (A) a live culture of cells and (B) corresponding transformed representations of the live cell images shown in A indicating regions with cells in grey. Images are shown for Day 2, Day 3, Day 4, Day 5, Day 6, and Day 7 as annotated.

FIG. 4A shows images taken daily of a culture of cells within the wells of a cell culture vessel. Visual inspection of the images confirms that the confluence of the culture of cells increases from a first (earlier) time point compared to a subsequent one or more time points, but the confluency and change thereto is difficult to efficiently and reliably quantify. FIG. 4B shows transformed representations of each image shown in FIG. 4A. Based on the transformed representations, at least one processor 600 of system 1 may readily calculate the confluency of the culture of cells within a cell culture vessel or between cell culture vessels, whether at a single time point or across multiple time points.

Figure 5:
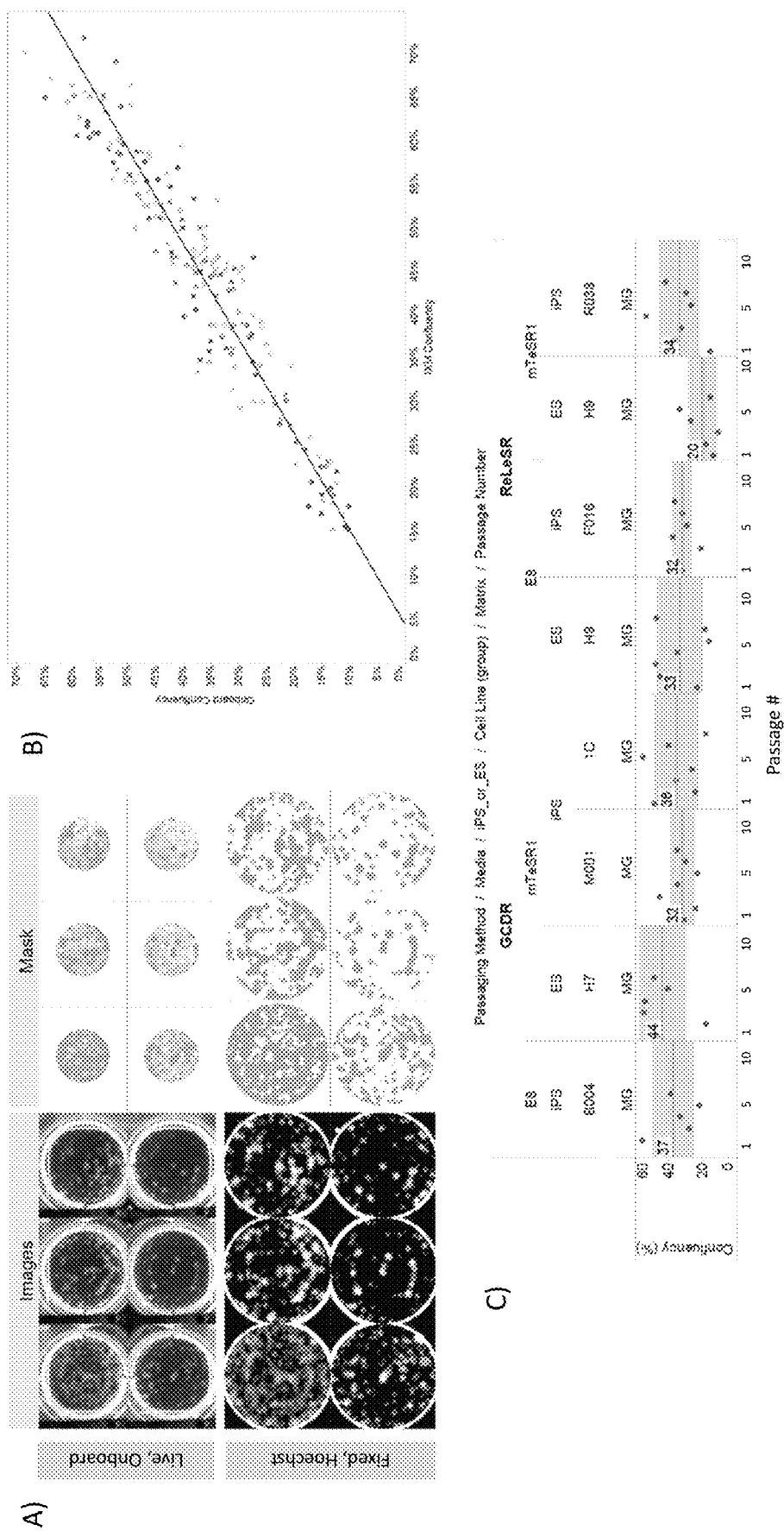
FIG. 5 shows that confluency of cultures of cells may be determined based on the one or more images captured by the imaging module. (A) Visual comparison of confluency of a live cell imaged culture of cells using the onboard imaging module and the corresponding transformed representation to a culture of cells stained using Hoechst and imaged using fluorescent microscopy (Hoechst 33258, 352 nm excitation, 461 nm emission). (B) A regression analysis of % confluency as determined by either live cell imaging 194 cultures of cells using the imaging module wells or Hoechst-staining the same 194 cultures. Each dot represents one cell culture vessel (i.e. a well of a 6-well plate). (C) A chart summarizing determinations of % confluency of one well of a variety of indicated cell-types cultured under a variety of indicated conditions over consecutive passages. The variety of indicated conditions include Gentle Cell Dissociation Reagent (GCDR™) (STEMCELL Technologies) or ReLeSR™ (STEMCELL Technologies) based clump generation, TeSR-E8™ (STEMCELL Technologies) or mTeSR1™ (STEMCELL Technologies) maintenance media, iPS or ES cell lines, and various cell lines.

Determinations of confluency based on the transformed representations are in agreement with confluency determinations using classical approaches with DNA binding dyes, such as Hoechst staining (FIGS. 5A and 5B). FIG. 5A compares actual images and transformed representations of the same cell culture vessel either unstained or stained with Hoechst. FIG. 5B verifies by regression analysis the concordance of the calculated confluencies of the cultures of cells using the two methods ($R^2=0.9$, standard error=0.04, p=0.95). FIG. 5C establishes that confluency of a culture of cells over a series of time points can be calculated based on the one or images for various cell lines cultured under diverse conditions.

Figure 6:
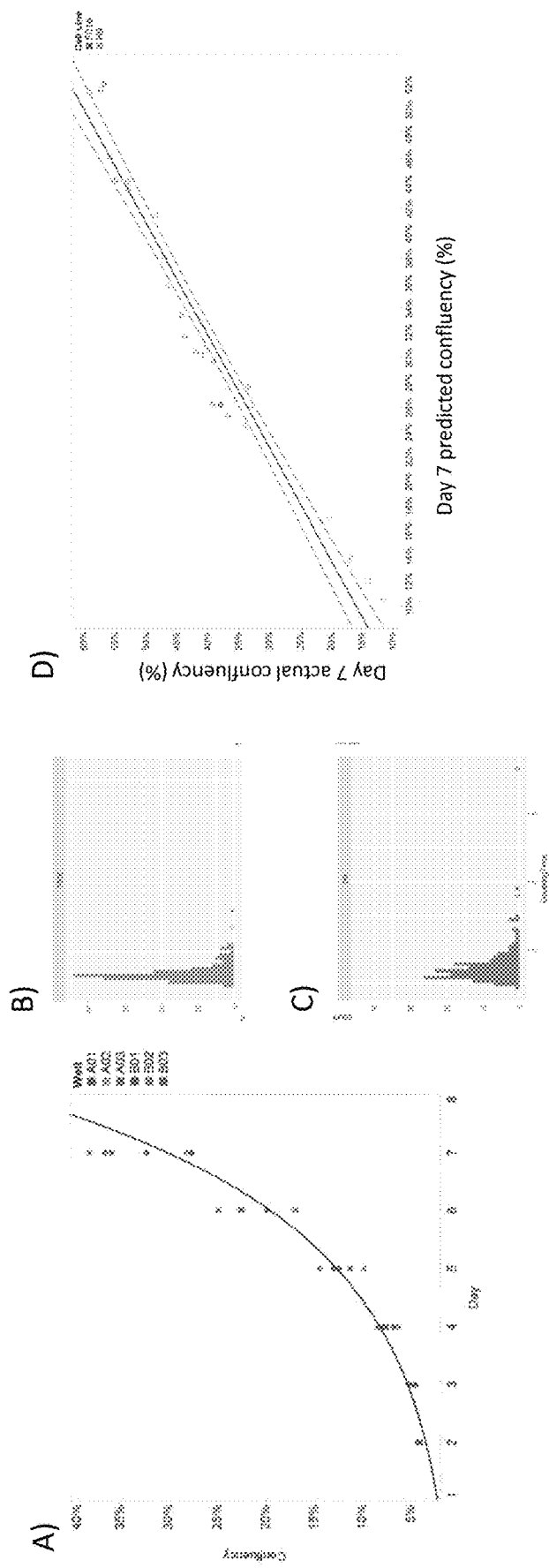
FIG. 6 shows various ways in which a determination of % confluency over more than one time point may be exploited. (A) Shows a graph wherein the % confluency of 6 cultures of cells (i.e. each well of a 6-well plate) is fit to an exponential growth model. (B) Shows a histogram wherein % confluency and the exponential fitting may be used to calculate the doubling time for 162 cultures of F016 cells (mean=33.1 hours, stdev±7.2 hours). (C) Shows a histogram wherein % confluency and the exponential fitting may be used to calculate the doubling time for 186 cultures of H9 cells (mean=37.9 hours, stdev±14.9 hours). (D) Shows a regression analysis of predicted day 7 confluency and actual 7-day confluency ($R^2$=0.95). Predicted day 7 confluency was determined by fitting day 2 to day 6% confluency data to an exponential growth model, as in (A).
Figure 7:
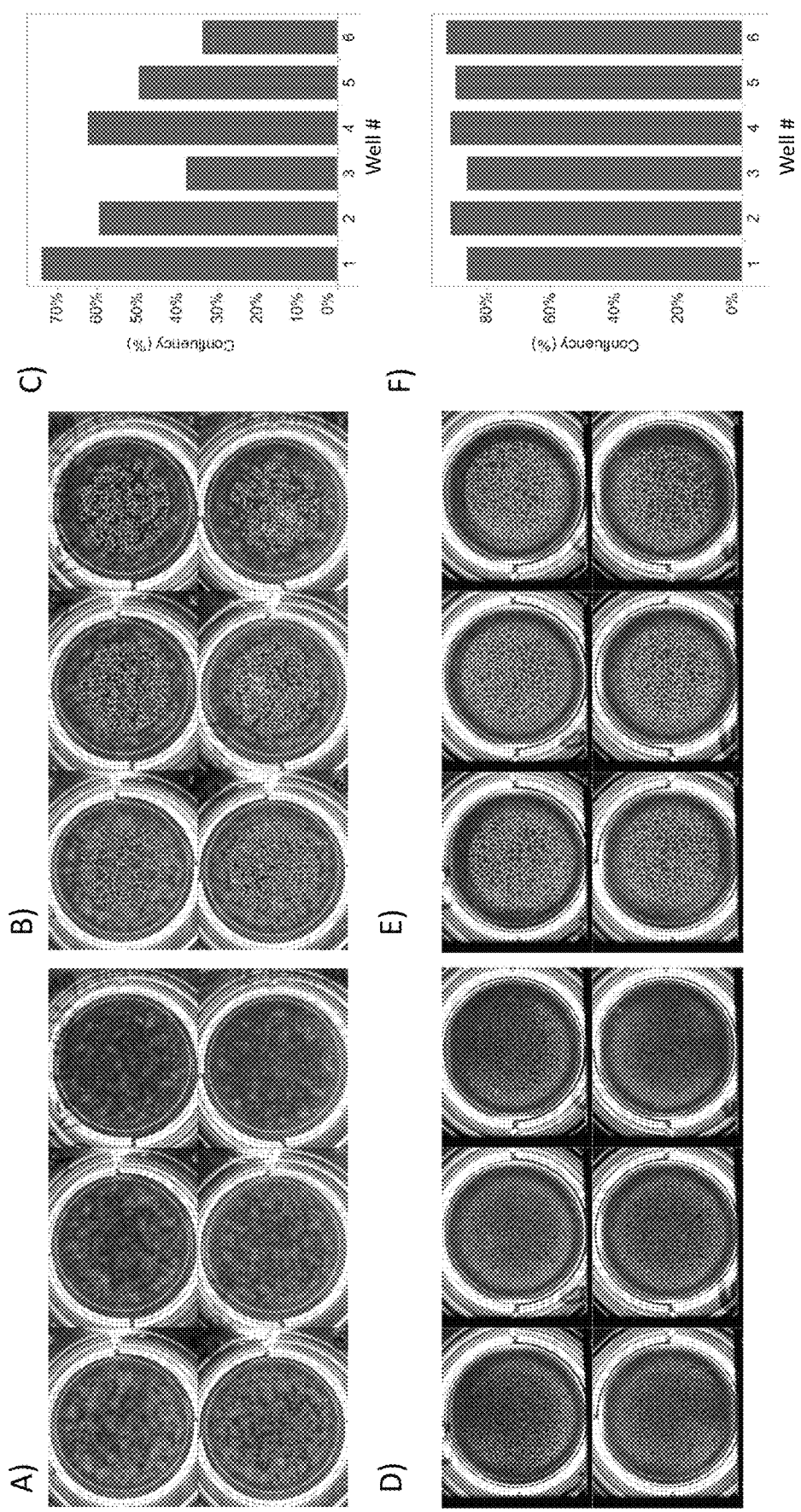
FIG. 7 shows % confluency may be calculated from one or more images of spray passaged cells and single cell passaged cells. (A) shows a representative image of each well of a 6-well culture plate of spray passaged H9 cells. (B) shows the corresponding masked region of each well in (A). (C) shows the corresponding % confluency values after image analysis of the masked regions in (B). (D) shows a representative image of each well of a 6-well culture plate of single-cell passaged M001 cells. (E) shows the corresponding masked region of each well in (D). (F) shows the corresponding % confluency values after image analysis of the masked regions in (E).

Further, determinations of confluency at different time points based on the transformed representations confirm that increased confluency of a culture of cells fits approximately an exponential growth model (FIG. 6A), consistent with the expected growth rate of cells in culture. The determination of the change in confluency may also be used to calculate the growth rate (i.e. doubling time) of a culture of cells. FIGS. 6B and C show for two different cultures of cells (i.e. cell lines) that the calculated doubling time is consistent with expected values. Based on the exponential growth model determined from the change over time of the confluency of a culture of cells, it was possible to predict the confluency of a culture of cells at a subsequent time point (FIG. 6D). FIG. 6D confirms that the predicted confluency at the subsequent time point accords with the actual confluency of the same culture of cells at the same subsequent time point.

Whereas the foregoing demonstrates that confluency may be calculated based on one or more images of a culture of cells that are clump passaged, it is also possible to calculate the confluency of a culture of cells that are either spray passaged (cells detached via repeated washing of culture media over the culture of cells, without mechanical scraping) or passaged as single cells (FIG. 7A-F). Thus, the automated systems and methods disclosed herein may be applicable to cells that are not necessarily passaged/cultured as clumps, such as mammalian cells in general, including but not limited to certain PSC lines, mesenchymal stem cells, epithelial stem cells, neural stem cells, cancer cells, cancer cell lines, etc. In embodiments where PSC are passaged as single cells, it may be necessary to include in a culture medium a supplement that promotes the survival of individual PSC, such as CloneR™ (STEMCELL Technologies) or others that may be disclosed and/or commercially available. Thus, it may be possible to use automated system 1 to derive a clonal population of cells.

In one embodiment the one or more characteristics correspond to a measure of the cell number within a cell culture vessel. The number of cells within a culture of cells, such as those organized into colonies, may be a function of at least the area of individual cells, the area of the colony the individual cells are comprised in, and/or the degree of cell stacking within the colony. While in many cases the area of an individual cell of interest may already be known, each of an area of an individual cell and a colony of cells and the degree of cell stacking may be calculated from the one or more images captured using imaging module 100. Indeed, a greater colony area and a high degree of cell stacking in a cell colony should correspond to an increase in the number of cells in that colony, and consequently an increase in the number of cells in a culture of cells.

Whereas colony area may be calculated based on the raw images or the transformed representations of the one or more images, quantifying the degree of cell stacking poses a bigger challenge. The degree of cell stacking may be determined based on the brightness of individual colonies, since with increased layering of cells less light is able to pass therethrough, resulting in a relatively brighter colony. In one embodiment the transformed representation may be presented as a heat map from which the degree of cell stacking may be determined. In one embodiment raw image of the one or more images may provide sufficient data with regard to colony apparent brightness. In any event, having obtained the necessary values the number of cells in a cell culture vessel (or in each of the colonies therein) may be calculated. In embodiments where a particular culture of cells is not prone to cell stacking, then the cell number may be calculated without reliance on a determination of the brightness of the individual colonies of a culture of cells.

Figure 8:
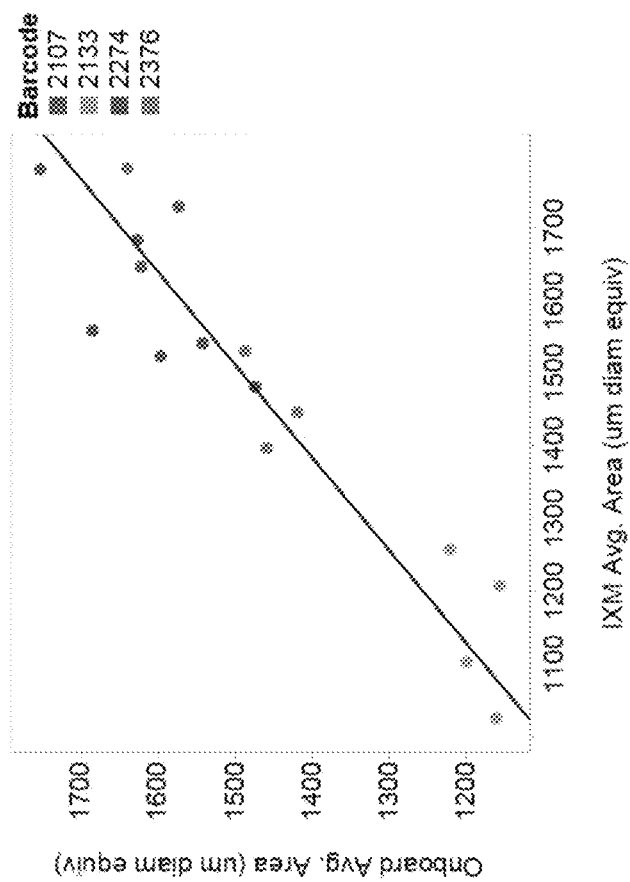
FIG. 8 shows a regression analysis of average colony area of the cultures of cells of 24 wells (i.e. each well of a 6 well plate) calculated based on the one or images captured by the image module and average colony area as determined for same cultures of cells by Hoechst staining protocols ($R^2=0.86$, p=0.94).

In FIG. 8 it is shown that average colony size (i.e. area) calculated based on the one or more images corresponds to the average colony size (i.e. area) determined using a Hoechst staining approach ($R^2=0.86$, p=0.94). Thus, a measure of colony size distribution within a culture of cells (or between multiple cultures of cells) may be determined from the one or more images, and such one or more characteristics may be used alone or in combination with any other one or more characteristics to effect an operation of system 1.

Figure 9:
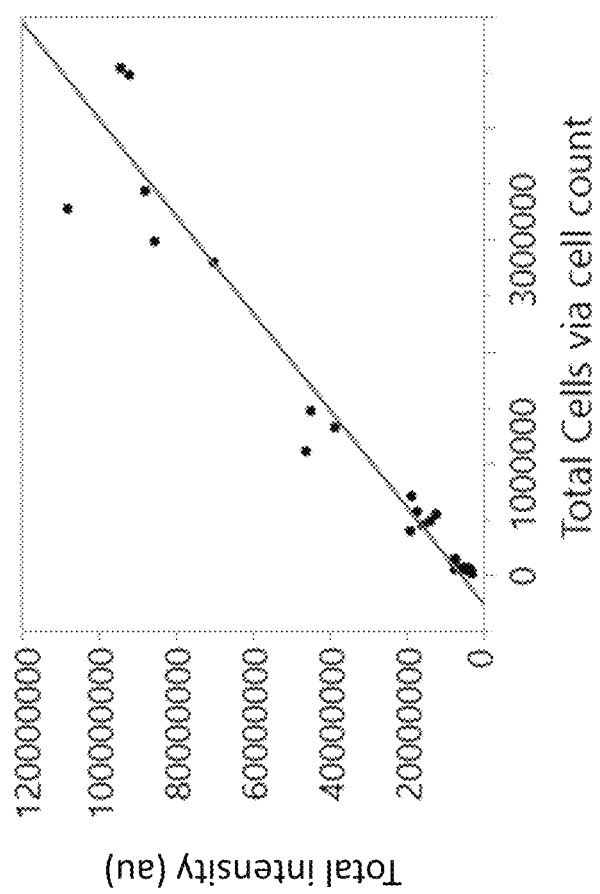
FIG. 9 shows a regression analysis of the total intensity (arbitrary units) within 24 cultures of cells as calculated based on the one or images captured by imaging module and actual number of cells within same cultures of cells ($R^2=0.94$, p<0.0001). Total intensity is defined as the sum of the intensities of each pixel within the masked region of the image. To generate actual cell counts, all cells were harvested from the culture vessel and used to generate a single cell suspension, which was then sampled for counting.

In FIG. 9 it is shown that total cell number within a cell culture vessel may be calculated based on the one or more images captured using image module 100, and that such calculation shows a good correlation with counts of total cell number obtained using a manual approach ($R^2=0.94$, p<0.0001). A determination of total cell number based on the one or more images is expressed in terms of raw intensity density, wherein the raw intensity density value is generated from the transformed representation of cell confluency in combination with the one or more images of a live culture of cells (i.e. raw images).

In one embodiment, the one or more characteristics may correspond to a measure of the morphology of the culture of cells within the cell culture vessel. An acceptable or unacceptable morphology of the culture of cells may be determined by comparing a digital profile of the culture of cells, based on the one or images, against a known standard. For example, a PSC colony is typically domed with smooth edges, exhibits tight packing of cells and high nuclear to cytoplasmic ratios. In contrast, differentiated PSC colonies or those PSC colonies undergoing differentiation deviate from the foregoing characteristics. Accordingly, a digital profile of the PSC colonies in a culture of cells can be generated based on the one or more images and upon comparison to a standard, system 1 may execute via the at least one processor an appropriate course of action.

In an embodiment related to the above paragraph, the one or more characteristics may correspond to a measure of the degree of differentiation of the culture of cells within the cell culture vessel. Based on the one or more images, the concordance or discordance of the morphology of a culture of cells (such as on a per colony basis or on an average basis) in comparison to a standard may be predictive of the differentiation status of the culture of cells. For example, if a differentiation protocol is in progress using automated system 1 and the calculated one or more characteristics confirm expected cell morphologies at a particular point in time, then no deviation from the protocol then in progress may be necessary. However, if less than expected or no differentiation is determined based on the calculated one or more characteristics, then system 1 may permit the protocol to continue for a further one or more imaging time points, or system 1 may perform a media change to introduce fresh differentiation medium. In another example, if the automated system 1 is executing an expansion protocol or a maintenance protocol of a culture of PSC, then significant degrees of differentiation may trigger an earlier than anticipated passaging protocol or a termination protocol.

Figure 10:
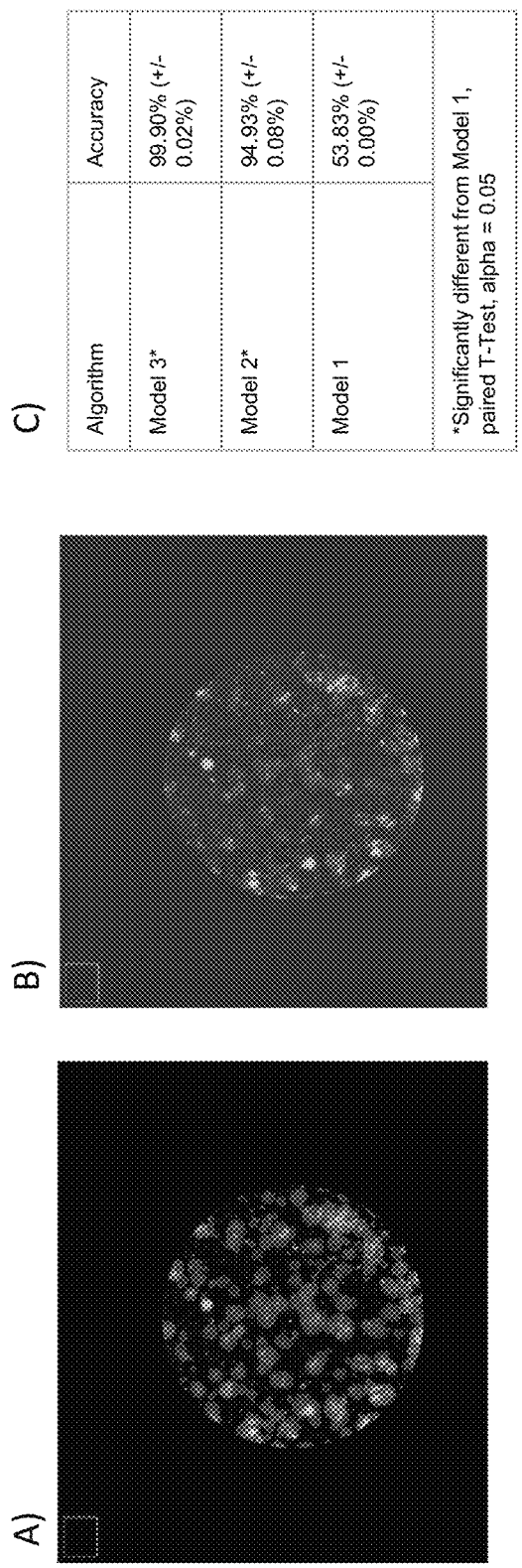
FIG. 10 shows the results of machine learning algorithms applied against a set of images captured by the imaging module. (A) Shows a representative image of a culture of cells as captured by imaging module after cropping. (B) Shows an overlay of automatically classified regions of background (darkest), differentiated (brightest), and undifferentiated (intermediate) regions of the representative image shown in (A). (C) Shows the results of three different classification models. Model 3 classifies all pixels as the most common class i.e. undifferentiated, and is included as a control.

In one embodiment, the differentiation status (or a change in morphology) of a culture of cells may be determined with reliance on the one or more images and an equation or model derived from data obtained using a machine learning classifier (i.e. a trained machine learning classifier). FIGS. 10A and 10B show a representative image as captured by imaging module 100 and a representative image of an overlay of undifferentiated, differentiated (brighter) and background (darkest) regions of the image in 10A, respectively. FIG. 10C shows the results of a classifier using three different classification models. Using a first classification model which relies only on classifying undifferentiated colonies, while ignoring predictors, a 53.83%±0.00% classification accuracy could be achieved. Using a second classification model which assigns features to classes (i.e. undifferentiated, differentiated, and background) having the highest correlation, a 94.93%±0.08% classification accuracy could be achieved. Using a third classification model which assigns features to classes (i.e. undifferentiated, differentiated, and background) based on a decision tree of rules, a 99.90%±0.02% classification accuracy could be achieved. The classifier used to generate the foregoing data was trained using a set of images wherein regions of background, undifferentiated PSCs, and differentiated PSCs were manually selected in a subset of one or more images. This training set did not include the test image in FIG. 10. Classifier training and experimentation was performed using WEKA Workbench. See, e.g., Ian H. Witten and Eibe Frank (2005) "Data Mining: Practical machine learning tools and techniques", 2nd Edition, Morgan Kaufmann, San Francisco, 2005.

Since ectodermal, endodermal and mesodermal lineage cells each exhibit unique morphologies, it would also be possible for a trained machine learning classifier to make such distinctions based on the one or more images.

Figure 11:
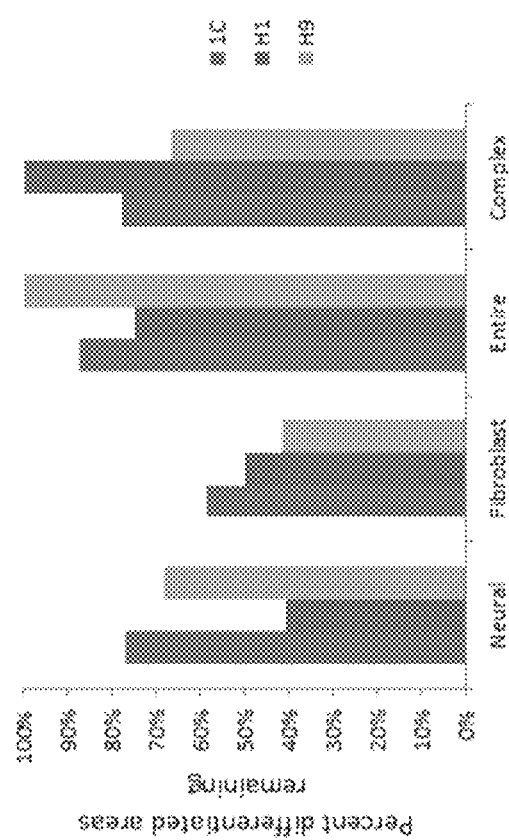
FIG. 11 shows percent differentiated areas remaining in cultures of 3 different cell lines after an automated passaging protocol using ReLeSR™ (STEMCELL Technologies). For each cell line, 6 different wells were assessed for neural-like colonies, fibroblast-like colonies, fully differentiated colonies (entire), and complex differentiated colonies.

In embodiments where the systems or methods disclosed herein are used to carry out a PSC maintenance protocol, it may also be possible to selectively passage undifferentiated PSC, thus leaving behind in the cell culture vessel colonies that exhibit relatively high degrees of differentiation (FIG. 11). For example, at such time when system 1 initiates a passaging protocol in response to commands initiated by at least one processor 600, pipette module 200 may aspirate the cell culture medium from the cell culture vessel (with or without reliance of tilting function of stage module 500) and liquid dispenser module 300 may dispense a volume of wash buffer into the cell culture vessel (which wash buffer is subsequently aspirated using pipette module 200). A specialized cell detachment solution, such as ReLeSR™ (STEMCELL Technologies), may be dispensed into the cell culture vessel to selectively detach colonies of undifferentiated PSC from the cell culture vessel. Depending on the measure of differentiation of a culture of cells, the time of exposure to the cell detachment solution may be adjusted. For example, in the case of high estimated differentiation a shorter incubation time may reduce the proportion of differentiated colonies that become detached. Thus, seeding a volume of a suspension of cells generated from only the detached colonies of undifferentiated PSC may enrich for undifferentiated PSC in a daughter cell culture vessel. Likewise, in carrying out a differentiation protocol, thusly detached colonies of undifferentiated PSC may be discarded and the remaining differentiated colonies may be dissociated and then passaged.

In one embodiment, the one or more characteristics may correspond to a measure of the change of the calculated one or more characteristics from a first time point compared to one or more subsequent time points. For example, the one or more characteristics may be a measure of the confluence of the culture of cells at a first time point as compared to a measure of the confluence of the culture of cells at a second time point.

Figure 12:
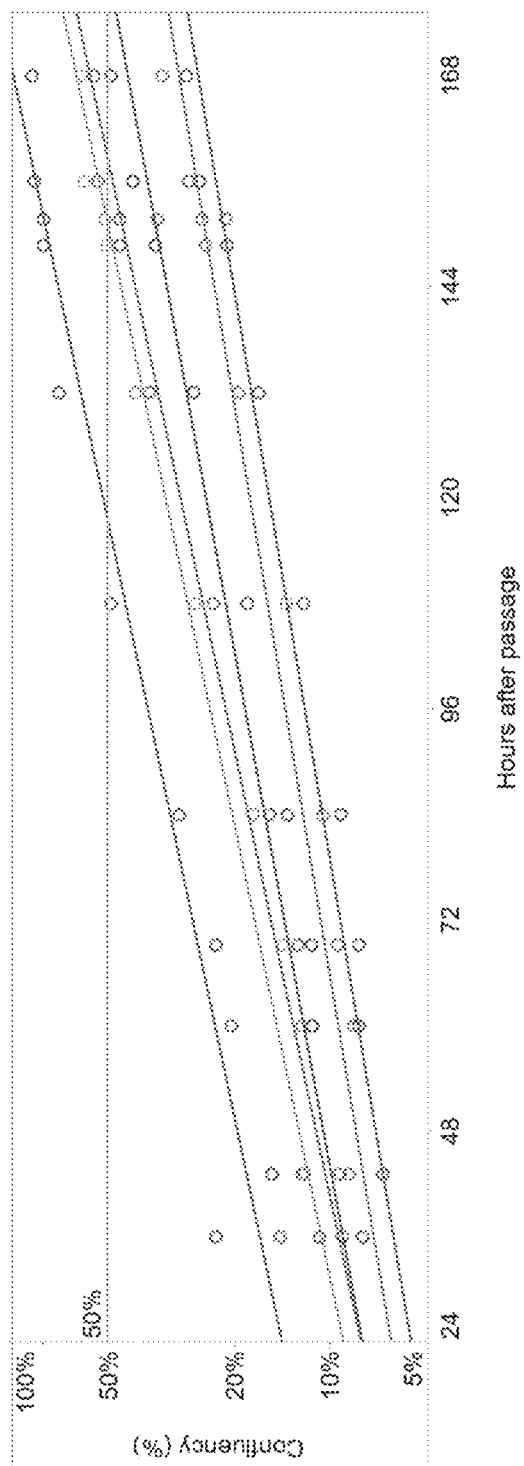
FIG. 12 shows a graph wherein a calculation of the % confluency of a culture of cells at more than one earlier time point may be used to predict the time when the culture of cells will reach a desired % confluency with high temporal resolution. Each line corresponds to a different cell culture vessel (i.e. well of a 6-well plate).

FIG. 12 shows that the time at which a passaging protocol is to be executed using automated system 1 may be determined based on calculating the confluency of a culture of cells at a first time point and at one or more subsequent time points. Thus, extrapolating plots of the foregoing data to a maximum or desired pre-passage confluency for any culture of cells may assist with scheduling a passaging protocol, particularly when automated system 1 is responsible for up to hundreds of plates at any one point in time.

In one embodiment the one or more characteristics may correspond to a measure of one of the one or more characteristics as a function of a different one of the one or more characteristics. For example, the one or more characteristics may be a measure of the confluence of the culture of cells as a function of the degree of differentiation of cells or colonies of the culture of cells, or vice versa. Such of the one or more characteristics may also be assessed at a first time point and at one or more subsequent time points.

Based on the acquisition and analysis of all the data points associated with the calculations of the one or more characteristics, system 1 is capable of self-learning (i.e. self-training), and does not require an operator to provide instructions regarding when to execute an automated passaging, or other, protocol. Thus, the subject matter disclosed herein may relate to systems and methods for adaptively passaging a culture of cells.

Where used herein, "adaptively passaging" refers to a passaging protocol that is flexible and the execution of which relies on the calculated one or more characteristics based on one or images captured at one or more time points. Further, such a passaging protocol does not necessarily rely on cues from an operator of system 1. Rather, system 1 having processed the one or more images (captured at one or more time points) and calculated the one or more characteristics, may execute a passaging protocol (or an expansion protocol, or a differentiation protocol) at an appropriate time and with an appropriate quantity of cells with a view to obtaining or maintaining consistent cultures of cells during each subsequent passage, such as but not limited to during routine maintenance culture of a culture of cells or during an onboarding operation of a newly-derived or—obtained cell line.

In one embodiment, the one or more characteristics calculated in respect of the culture of cells in the cell culture vessel and a second culture of cells in a second cell culture vessel is different at a first time point or at the one or more subsequent time points, and based on the operation of system 1 the one or more characteristics become more consistent during a subsequent passage. For example, if the confluence of the first culture of cells in the first cell culture vessel, or in a first well thereof, is 25% at a first time point (e.g. 6 days into passage 0) and the confluence of the second culture of cells in the second cell culture vessel, such as in a second well of the first cell culture vessel, is 10% at the first time point, this will result in the execution of asynchronous automated passaging protocols. Executing asynchronous automated passaging protocols may be undesirable for matters of efficiency, but may also expose one culture of cells to unnecessary risks as the other culture of cells is being passaged, if for example the first culture of cells and the second culture of cells are in different wells of the same cell culture vessel. Thus, automated system 1 may adaptively adjust one or more elements of a subsequent passage of both the first and second cultures of cells, such as the seeding density, in order to make the confluence of the first and second cultures of cells more consistent at a subsequent time point (e.g. 6 days into passage 0+n).

Figure 13:
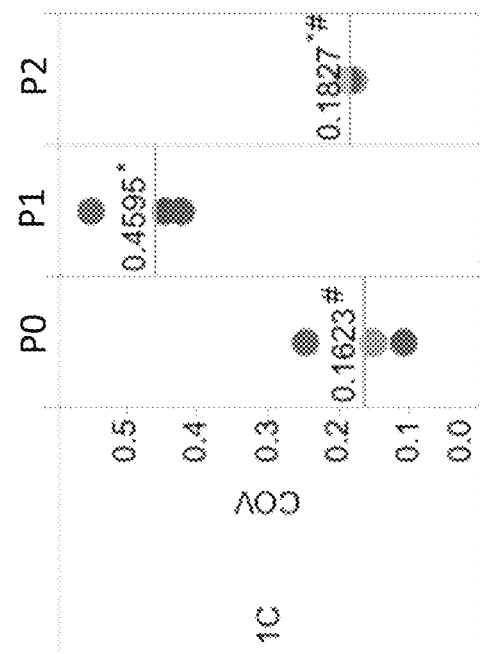
FIG. 13 shows a dot plot of the coefficient of variation within the 6-wells of a 6-well plate of Day 7% confluency of 1C cells at 3 consecutive passages. Adaptive passaging based on calculated % confluency can lead to more consistent % confluency of cultures of cells at a subsequent time point. Based on a Wicoxon Signed-Rank Test for Paired Samples no significant difference in the coefficient of variation between P0 and P2 was observed, in contrast to P1 and P2. At P0 all wells for a given plate were seeded with the identical volume. At P1 the wells were passaged using dilutions ranging from 1:25 to 1:200, resulting in an increased COV. At P2, using a regression model for adaptive passaging, split ratios were chosen for each well so that the wells would revert back to having similar confluency.

FIG. 13 shows that across a number of cell culture vessels having a relatively wide variation of the confluence of the respective cultures of cells therein, the variation of confluence can become more consistent following an adaptive passaging protocol using system 1. Having determined the relationship between confluency of the parent cell culture vessel and the confluency of the daughter cell culture vessel, it is possible to calculate an appropriate dilution (i.e. seeding density) of a cell suspension into a daughter or granddaughter cell culture vessel.

The at least one processor of system 1 is further configured to execute an automated passaging protocol to passage the culture of cells, the protocol including coordinating operation of at least imaging module 100, pipette module 200, liquid dispenser module 300, and handling module 400 based on comparing the calculated one or more characteristics of the culture of cells and a learned or an inputted threshold level for the one or more characteristics of the culture of cells.

Upon capturing the one or more images, automated system 1 calculates (by the at least one processor 600 communicatively coupled to the imaging module) one or more characteristics of the culture of cells based on the one or more images. In one embodiment, calculating the one or more characteristics may be accomplished in accordance with the description provided above. Specifically, the one or more characteristics may include:
  a) a measure of the confluence of the culture of cells;
  b) a measure of the morphology of cells or colonies of the culture of cells;
  c) a measure of the differentiation of cells or colonies of the culture of cells;
  d) a measure of colony size distribution of the culture of cells;
  e) a measure of the change of a), b), c), or d) from the first time point to the one or more subsequent time points; or
  f) a measure of a) relative to b), c) or d), a measure of b) relative to a), c), or d), a measure of c) relative to a), b), or d), or a measure of d) relative to a), b), or c).

Having calculated the one or more characteristics, automated system 1 executes (by the at least one processor 600) an automated passaging protocol based on comparing the calculated one or more characteristics of the culture of cells to a learned or inputted threshold level of the one or more characteristics of the culture of cells.

In one embodiment, the learned or the inputted threshold level in respect of the measure of a confluence of a culture of cells (i.e. cell or colony) is in a range of about 30-90%. Thus, if the culture of cells has achieved between about 30-90% confluence, automated system 1 may initiate a passaging protocol. In one embodiment the measure of a confluence of a culture of cells (i.e. cell or colony) is in a range between about 40-80%. In one embodiment the measure of a confluence of a culture of cells (i.e. cell or colony) is in a range between about 50-70%.

In one embodiment, the learned or the inputted threshold level in respect of the measure of a morphology of a culture of cells (i.e. cell or colony) is about ±30% of a control cell culture. Thus, if the culture of cells has deviated, in terms of its morphology, between about ±30% of a control cell culture, automated system 1 may initiate a passaging protocol. In one embodiment the measure of a morphology of a culture of cells (i.e. cell or colony) is between about ±20% of a control cell culture. In one embodiment the measure of a morphology of a culture of cells (i.e. cell or colony) is between about ±10% of a control cell culture.

In one embodiment, the learned or the inputted threshold level in respect of the measure of a differentiation level of a culture of cells (i.e. cell or colony) is between about 0 to 30% of a control culture in a maintenance protocol or between about 50% to 100% of a control culture in a differentiation protocol. On the one hand, if the culture of cells has achieved a differentiation level of between about 0 to 30%, or between about 10-20%, or about 15% relative to a control culture in a maintenance protocol, automated system 1 may initiate a passaging protocol. In contrast, if the culture of cells has achieved a differentiation level of between about 0 to 30%, or between about 10-20%, or about 15% relative to a control culture in a differentiation protocol, automated system 1 may not initiate a passaging protocol. Rather, in such scenario automated system 1 may do nothing or replace spent differentiation medium with fresh differentiation medium. On the other hand, if the culture of cells has achieved a differentiation level of between about 50 to 100%, or between about 60 to 90%, or between about 70 to 80%, or about 75% relative to a control culture in a differentiation protocol, automated system 1 may initiate a passaging (and/or expansion) protocol or harvest the differentiated cells for downstream applications. In contrast, if the culture of cells has achieved a differentiation level of between about 50 to 100%, or between about 60 to 90%, or between about 70 to 80%, or about 75% relative to a control culture in a maintenance protocol, automated system 1 may initiate a passaging protocol to try and rescue the culture of cells or a termination protocol.

In one embodiment, the learned or the inputted threshold level in respect of the measure of colony size distribution of a culture of cells (i.e. cell or colony) is within about 20%, or about 15%, or about 10%, or about 5% of a mean colony size distribution of a control culture, or a subfraction thereof. Thus, if the culture of cells has achieved a mean colony size distribution within about 20%, or about 15%, or about 10%, or about 5% of a mean colony size distribution of a control culture, or a subfraction thereof, automated system 1 may initiate a passaging protocol. In one embodiment, the threshold level of within about 20%, or about 15%, or about 10%, or about 5% of a mean colony size distribution of a control culture pertains to a subfraction of the colony size distribution, for example the top 10%, or top 20% or top 30% or top 40%, or bottom 10%, or bottom 20%, or bottom 30%, or bottom 40%.

System 1 may further comprise an enclosure 700 to house at least pipette module 200, liquid dispenser module 300, handling module 400, and stage module 500, and also pipette tip racks 225 and 230, and carriage 220 in embodiments in which they are included. Imaging module 100 and camera 105 may also be housed in enclosure 700 (FIG. 3B), but may be included elsewhere, such as in an incubator module (described below).

In one embodiment, enclosure 700 maintains a sterile internal environment. In one embodiment, enclosure 700 may correspond to a sterile room. In such an embodiment, all of the modules of system 1 disclosed herein could be included in the sterile room. In one embodiment, enclosure 700 may correspond to a biological safety cabinet. In such an embodiment, due to space constraints, the modules localized therein should be limited to those that carry out the automated passaging (or otherwise) protocol.

In one embodiment, the more than one solution reservoirs 350, a refrigeration module 800, and a waste reservoir 900 are external of enclosure 700.

System 1 may further comprise a refrigeration module 800 to store one or more of the more than one solution reservoirs 350. Refrigeration module 800 is intended to store one or more of the more than one solution reservoirs 350 at a desired temperature. For example, a cell culture medium may be stored at about 4° C. in order to limit the degradation of the contents thereof. Similar, cell detachment solutions, wash buffers, and certain cell culture matrix solutions may desirably be stored at about 4° C.

Refrigeration module 800 may include one or more sensors. In one embodiment, a first sensor detects and reports (to at least one processor 600) on the mass of each of the more than one solution reservoirs 350. Thus, the first sensor provides real-time feedback to system 1 that an appropriate volume of solution has been discharged from the first reservoir. Failing which, system 1 may determine a corrective volume of solution to be dispensed from the first reservoir. In the same or a different embodiment, a second sensor detects and reports (to at least one processor 600) on the temperature within refrigeration module 800. Thus the second sensor provides real-time feedback to system 1 that refrigeration module 800 is maintained at an appropriate temperature.

System 1 may also include waste reservoir 900 (see FIG. 1). Waste reservoir 900 may be in fluid communication with a waste trough 925 located within enclosure 700. To minimize the chances of contaminating a culture of cells or other components within system 1, whether with undesired solutions or microorganisms, the design and location of the waste trough are important considerations. FIGS. 14A and 14B show one embodiment of waste trough 925.

In one embodiment the waste trough 925 may be remote from imaging module 100, liquid dispensing module 300, and stage module 500. In one embodiment, the waste trough 925 may be located beneath liquid dispenser module 300 to simplify disposal of cell culture solutions from the one or more conduits of liquid dispenser module 300 during priming operations (i.e. clearing old or room temperature solutions from the conduits).

Waste trough 925 comprises a channel 930 for conveying a solution into waste reservoir 900. In one embodiment waste trough comprises a first sink 935 and a second sink 937, both the first and second sinks in fluid communication with channel 930. First sink 935 may receive a discharge from pipette module 200, and second sink may receive a discharge from liquid dispenser module 300, and more particularly from the more than one conduits associated therewith.

In one embodiment, first sink 935 further comprises a flush inlet 938 for providing a solution, such as a sterilization solution. The person skilled in the art will be aware of appropriate sterilization solutions useful in cell culture processes. For example, the sterilization solution may be diluted bleach. Alternatively, the sterilization solution may be an alcohol, such as isopropyl alcohol.

In one embodiment, waste trough 925 may incorporate a geometry that minimizes the pooling of solutions discharged therein. In one embodiment, a receiving surface 940 of waste trough 925 may be downwardly sloped toward and urge discharged solutions through channel 930. In one embodiment, receiving surface 940 may further comprise a pair of sloped walls that converge to a point, or substantially a point, formed in receiving surface 940. In such an embodiment, the convergent pair of walls cooperating with the downward slope to urge discharged solutions toward and through channel 930.

In one embodiment waste trough 925 further comprises a liquid level sensor 945 to detect and report (to at least one processor 600) on waste reservoir 900 back-up or on blockage of channel 930.

In one embodiment, waste trough 925 may be coated with a hydrophobic coating or a superhydrophobic coating. In one embodiment, the coating may be silica nanoparticle-based. The person skilled in the art will be aware of other appropriate hydrophobic or superhydrophobic coatings, such as siloxanes or perfluorocarbon-based coatings, etc.

In one embodiment waste trough 925 may occupy a relatively small footprint in order to minimize large open areas where residual solutions, such as cell culture media, could collect and give rise to potential contamination problems. In one embodiment, waste trough 925 further comprises a cover 950 to further reduce open areas while not reducing its capacity.

System 1 may further comprise an incubator module 1000, wherein the incubator module maintains permissive environmental conditions for the culture of cells, such as pluripotent stem cells. Incubator modules are known in the art and may be purchased from, for example, Liconic. In one embodiment, incubator module 1000 may comprise racking for multiple cell culture vessels. In one embodiment, incubator module 1000 further comprises a handling means for selectively pulling a cell culture vessel from the racking, and such handling means selectively pulling the cell culture vessel based on a unique identifier associated with the cell culture vessel (i.e. bar code and bar code reader).

In one embodiment, incubator module 1000 includes one or more sensors to detect and report (to at least one processor 600) on the temperature therein, or such other condition such as humidity and other atmospheric conditions like $CO_2$%.

If system 1 comprises an incubator module 1000, it may be desirable to include a conveyor module 1150 to connect enclosure 700 and incubator module 1000 and for transporting the cell culture vessel from incubator module 1000 into proximity of handling module 400 (FIG. 1). In one embodiment, conveyor module 1150 may be closed to prevent exposure of the cell culture vessel to a non-sterile environment.

Both incubator module 1000 and conveyor 1150 are communicatively coupled to at least one processor 600. In respect of incubator module 1000, at least one processor 600 may initiate commands whether or not to: engage the handling means to selectively pull a cell culture vessel from or replace a cell culture vessel in the racking therein; or adjust the atmospheric conditions therein. In respect of conveyor module 1150, at least one processor 600 may initiate commands whether or not to: transport a cell culture vessel out of incubator module 1000; or transport a cell vessel into incubator module from, for example, enclosure 700.

System 1 may optionally further comprise a controller 700 for coordinating operation of each of the modules of the automated system. Controller 700 includes software that may be comprised in a personal computer. The software in controller 700 is capable of carrying out the commands needed to coordinate operation of each of the modules of the automated system.

System 1 may further comprise a graphical user interface 1200 communicatively coupled to the at least one processor. Graphical user interface 1200 is preferably located external of enclosure 700. In one embodiment, graphical user interface 1200 is a display of a personal computer integrated with system 1. In one embodiment, graphical user interface 1200 is a display of personal computer wirelessly connected to system 1. Graphical user interface 1200 may provide a user of system 1 with the necessary controls to direct the operation of system 1, such as to schedule automated cell culture processes, to review the automated cell culture processes executed by system 1, to review the one or more images captured by camera 105, to receive notifications from or the status of each of the sensors integrated into system 1, and to observe a fluid level report for each of the more than one solution reservoirs 350.

System 1 may further comprise a dissociation module 1300 in accordance with an apparatus for dissociating one or more colonies in a culture of cells as described herein below. Cell culture vessels may be transported to the dissociation module 1300 using handling module 300.

Methods of Using the System

Figure 15:
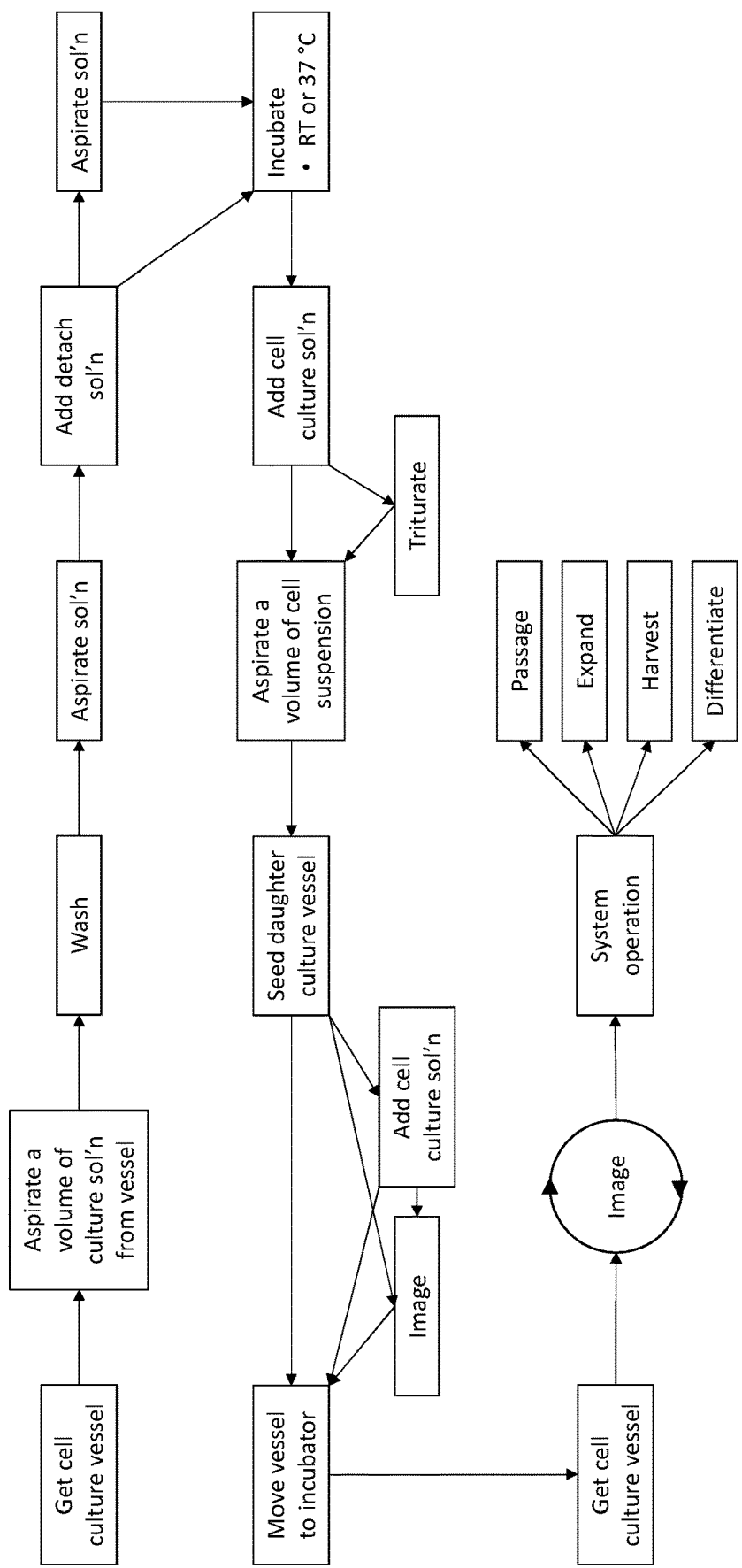
FIG. 15 shows a flow chart of one embodiment of a method for passaging a culture of cells.

In another aspect of this disclosure, automated system 1 may be used to carry out automated methods of passaging a culture of cells (FIG. 15). In one embodiment, automated system 1 may be used to carry out automated methods of adaptively passage a culture of cells. In specific embodiments, the cells may be pluripotent stem cells, and even more specifically the cells may be human pluripotent stem cells. Since it is desirable in many applications to passage human pluripotent stem cells as clumps or clusters, the automated methods for passaging a culture of human pluripotent stem cells may be suited to the clump passaging thereof.

The methods disclosed herein may be used to passage a culture of cells, however, they are not limited in this way. Variations of the methods may be employed to perform a medium exchange as part of a routine maintenance regime. Alternatively, the methods may be employed to perform a cell expansion regime, wherein the culture of cells may be successively cultured into larger culture vessels or into a greater number of wells. Alternatively, the methods may be employed to perform an onboarding regime of a new cell line, such as a newly-derived or—obtained PSC cell line, wherein acquisition and analysis of data (i.e. the one or more characteristics) at early passage(s) may inform on the optimal conditions for performing subsequent passages. Alternatively, the methods may be employed to perform a cell differentiation regime, wherein a starting population of cells is exposed to differentiation conditions, such as a differentiation medium, to convert the starting population of cells into a derivative lineage of cells. Examples specific to pluripotent stem cells include differentiation of such cells upon exposure to an appropriate culture medium into ectoderm-like or ectodermal cells, into endoderm-like or endodermal cells, or mesoderm-like or mesodermal cells.

The automated methods for passaging a culture of cells comprise providing the culture of cells in a cell culture medium within a cell culture vessel. In one embodiment, providing the culture of cells comprises conveying the culture of cells from an incubator. Conveying the cell culture vessel may be accomplished using a conveyor means, such as the conveyor module described hereinabove. In one embodiment, providing the cell culture vessel (and the culture of cells therein) may be accomplished using a cell culture vessel handler, such as the handling module described hereinabove.

In one embodiment, the automated methods, and more specifically providing the cell culture vessels (and the culture of cells therein), may further comprise positioning the culture vessel on a stage, such as the stage module described hereinabove. In one embodiment, positioning the cell culture vessel may be accomplished using the cell culture vessel handler (i.e. the handling module).

The automated methods also comprise capturing by an imaging module one or more images of the culture of cells at a first time point and at one or more subsequent time points. In one embodiment, the imaging module is essentially as described hereinabove.

Upon capturing the one or more images, the automated methods also comprise calculating by at least one processor communicatively coupled to the imaging module one or more characteristics of the culture of cells based on the one or more images. In one embodiment, calculating the one or more characteristics may be accomplished in accordance with the description provided above. Specifically, the one or more characteristics may include:

a) a measure of the confluence of the culture of cells;
b) a measure of the morphology of cells or colonies of the culture of cells;
c) a measure of the differentiation of cells or colonies of the culture of cells;
d) a measure of colony size distribution of the culture of cells;
e) a measure of the change of a), b), c), or d) from the first time point to the one or more subsequent time points; or
f) a measure of a) relative to b), c) or d), of b) relative to a), c), or d), of c) relative to a), b), or d), or of d) relative a), b), or c).

Having calculated the one or more characteristics, the automated methods also comprise executing by the one or more processors an automated passaging protocol based on comparing the calculated one or more characteristics of the culture of cells to a learned or inputted threshold level of the one or more characteristics of the culture of cells.

In one embodiment, the learned or the inputted threshold level in respect of the measure of a confluence of a culture of cells (i.e. cell or colony) is between about 30-90%. Thus, if the culture of cells has achieved between about 30-90% confluence, automated system 1 may initiate a passaging protocol. In one embodiment, the measure of a confluence of a culture of cells (i.e. cell or colony) is between about 40-80%. In one embodiment, the measure of a confluence of a culture of cells (i.e. cell or colony) is between about 50-70%.

In one embodiment, the learned or the inputted threshold level in respect of the measure of a morphology of a culture of cells (i.e. cell or colony) is between about ±30% of a control cell culture. Thus, if the culture of cells has deviated, in terms of its morphology, between about ±30% of a control cell culture, automated system 1 may initiate a passaging protocol. In one embodiment, the measure of a morphology of a culture of cells (i.e. cell or colony) is between about ±20% of a control cell culture. In one embodiment, the measure of a morphology of a culture of cells (i.e. cell or colony) is between about ±10% of a control cell culture.

In one embodiment, the learned or the inputted threshold level in respect of the measure of a differentiation level of a culture of cells (i.e. cell or colony) is between about 0 to 30% of a control culture in a maintenance protocol or between about 50% to 100% of a control culture in a differentiation protocol. On the one hand, if the culture of cells has achieved a differentiation level of between about 0 to 30%, or between about 10-20%, or about 15% relative to a control culture in a maintenance protocol, automated system 1 may initiate a passaging protocol. In contrast, if the culture of cells has achieved a differentiation level of between about 0 to 30%, or between about 10-20%, or about 15% relative to a control culture in a differentiation protocol, automated system 1 may not initiate a passaging protocol. Rather, in such scenario automated system 1 may do nothing or replace spent differentiation medium with fresh differentiation medium. On the other hand, if the culture of cells has achieved a differentiation level of between about 50 to 100%, or between about 60 to 90%, or between about 70 to 80%, or about 75% relative to a control culture in a differentiation protocol, automated system 1 may initiate a passaging (and/or expansion) protocol or harvest the differentiated cells for downstream applications. In contrast, if the culture of cells has achieved a differentiation level of between about 50 to 100%, or between about 60 to 90%, or between about 70 to 80%, or about 75% relative to a control culture in a maintenance protocol, automated system 1 may initiate a passaging protocol to try and rescue the culture of cells or a termination protocol.

In one embodiment, the learned or the inputted threshold level in respect of the measure of colony size distribution of a culture of cells (i.e. cell or colony) is within about 20%, or about 15%, or about 10%, or about 5% of a mean colony size distribution of a control culture, or a subfraction thereof. Thus, if the culture of cells has achieved a mean colony size distribution within about 20%, or about 15%, or about 10%, or about 5% of a mean colony size distribution of a control culture, or a subfraction thereof, automated system 1 may initiate a passaging protocol. In one embodiment, the threshold level of within about 20%, or about 15%, or about 10%, or about 5% of a mean colony size distribution of a control culture pertains to a subfraction of the colony size distribution, for example the top 10%, or top 20% or top 30% or top 40%, or bottom 10%, or bottom 20%, or bottom 30%, or bottom 40%.

Where used herein, "an automated passaging protocol" refers to the culturing activities up to a point in time when a culture of cells may be propagated, such as by sub-culturing, and the activities necessary for effecting the sub-culture of a culture of cells including seeding some or all of the culture of cells into one or more daughter cell culture vessels. Thus, the term passaging inclusively refers to the activities related to the routine culturing of cells, such as sub-culturing the culture of cells, and also to workflows aimed at expanding or differentiating a culture of cells.

In one embodiment, executing a passaging protocol may be accomplished by obtaining a suspension of cells from the culture of cells and seeding some or all of the suspension of cells in a daughter cell culture vessel.

In one embodiment, obtaining the suspension of cells further comprises passing the suspension of cells through a first pipette tip to dissociate the culture of cells into a single cells suspension or a plurality of clumps having an average diameter not exceeding a bore diameter of the first pipette tip. In one embodiment, passing the suspension of cells through the first tip may be performed using the pipette module as described hereinabove.

Prior to obtaining the cell suspension the culture medium in the first cell culture vessel may be removed by aspirating the culture medium from the cell culture vessel, or a well thereof. As above, aspirating the cell culture medium, in one embodiment, may be accomplished using the pipette module described hereinabove. In one embodiment, removing (i.e.) aspirating the cell culture medium may include tilting the first cell culture vessel followed by directing a pipette tip mated to a pipette of the pipette module into a lower corner of the cell culture vessel, or a well thereof.

After aspirating the culture medium, it may be desirable to perform a washing step by dispensing a wash buffer into the cell culture vessel, or a well thereof. In one embodiment, wash buffer may be dispensed using the liquid dispensing module described hereinabove. Thereafter, the wash buffer may be aspirated (i.e. removed) as described above, such as via the pipette module.

If a feeding regimen is being performed, fresh culture medium may be added (after aspirating spent culture medium and/or washing) to the cell culture vessel, or all appropriate wells thereof, prior to returning the cell culture vessel to an incubator, such as the incubator module described hereinabove.

In methods relating to passaging or expanding the cells, the culture of cells within the cell culture vessel having the cell culture medium removed therefrom (and optionally having undergone a wash step) may be contacted with a detachment/dissociation solution. Any appropriate detachment or dissociation solution may be used to contact the culture of cells in the cell culture vessel, or a well thereof. In one embodiment, the detachment solution may be ReLeSR™ (STEMCELL Technologies) or STEMdiff™ Neural Rosette Selection Reagent (STEMCELL Technologies). In one embodiment, the dissociation solution may be GCDR (STEMCELL Technologies) or some other trypsin-based solution. Contacting the culture of cells in the cell culture vessel with a detachment or dissociation solution may be carried out using the liquid dispensing module as described hereinabove. Depending on the type of solution used, the culture of cells may be incubated in the presence of the detachment or dissociation solution at about 37° C. or at room temperature for a sufficient period of time. Also depending on the type of solution used, it may be desirable to aspirate the solution prior to incubating the culture of cells. Further, depending on the type of solution used and on the cell type, it may be desirable to convey the cell culture vessel to the incubator module.

In one embodiment, the detachment solution is a fractionation solution, and the fractionation solution selectively detaches either a first population of differentiated cells or a second population of undifferentiated cells from a wall of the cell culture vessel. In such an embodiment, either ReLeSR™ (STEMCELL Technologies) or STEMdiff™ Neural Rosette Selection Reagent (STEMCELL Technologies) may be used, depending on the application.

Following the incubation of the first cell culture vessel, the next steps of the methods may comprise transporting the first cell culture vessel to the dissociation module (as described below) using the handling module and detaching a cell colony, such as but not limited to a pluripotent stem cell colony, from a bottom of the well of the first cell culture vessel using the dissociation module.

As mentioned above some or all of the one or more cell colonies may become detached due to the detachment/dissociation solution, or it may be necessary to urge some or all of the one or more cell colonies to detach using the dissociation module. In any event, activating the dissociation module may also aid in dissociating the detached cell colonies into a suspension of cells, and in one embodiment into a suspension of clumps of pluripotent stem cells.

In some embodiments, triturating the suspension of cells using the pipette module before or after activating the dissociation module may facilitate the dissociation of the one or more colonies into a suspension of cells, such as a suspension of clumps of pluripotent stem cells.

Following the dissociation of the one or more colonies into a suspension of cells, a volume of the suspension of cells (whether a single cell suspension or a suspension of a plurality of clumps) may be seeded into a daughter cell culture vessel, or a well thereof, such as with the pipette module.

In one embodiment, prior to or after seeding the volume of the suspension of cells into a daughter cell culture vessel, the automated methods may further comprise dispensing a first solution and second solution simultaneously or in sequence in the daughter cell culture vessel. In one embodiment, the first solution is the cell culture medium and the second solution is a solubilized extracellular matrix.

For an expansion experiment, some or all of the suspension of cells may be seeded into a second culture vessel that is larger than the first cell culture vessel, or into a plurality of wells of the second culture vessel.

Apparatus

Figure 16:
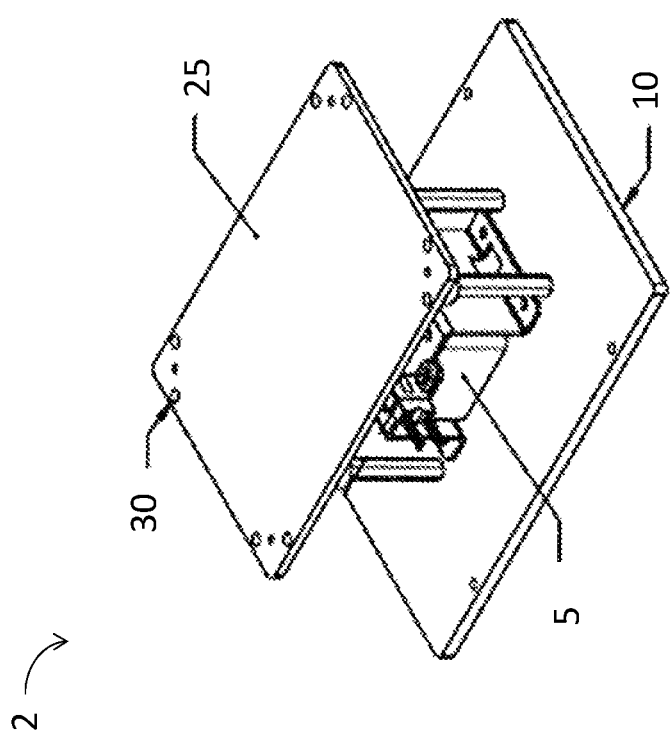
FIG. 16 shows a perspective view of the apparatus for dissociating one or more colonies present in a culture of cells.

In one aspect of this disclosure there is provided an apparatus for detaching or dissociating one or more colonies present in a culture of cells (see FIG. 16). Throughout this disclosure, apparatus 2 may also be referred to as a dissociation module.

As used herein, the term "cells" refers to any type of cell that is capable of being cultured, whether ex vivo or in vitro. It may be important that the cells grow as adhered cultures, but cells that grow in suspension are also within the scope of this disclosure. The cells may be mammalian in origin, and in some circumstances, the cells may be human cells. The cells may also be pluripotent stem cells, and in some embodiments, the cells may be human pluripotent stem cells. In some embodiments, the cells are one or more undifferentiated colonies in a culture of pluripotent stem cells. Undifferentiated pluripotent stem cells may be cultured as a monolayer or in suspension, and upon division they form colonies or aggregates, respectively. An undifferentiated pluripotent stem cell is a cell that is capable of self-renewal and may be differentiated to any lineage. For example, a pluripotent stem cell may be an embryonic stem cell, an induced pluripotent stem cell, or other types of cells emerging in the field, an example of which includes extended pluripotent stem cells. Many pluripotent stem cell lines are known, but it is routine to create new pluripotent stem cell lines using existing scientific technology.

Figure 17:
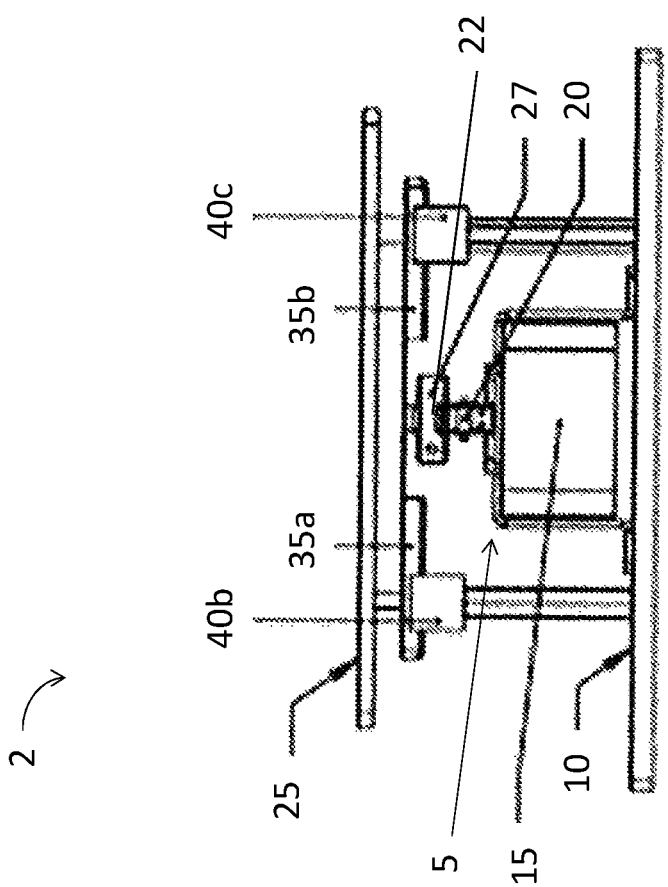
FIG. 17 shows a front view of the apparatus for dissociating one or more colonies present in a culture of cells.

In one embodiment of apparatus 2 for dissociating one or more colonies in a cell culture, the apparatus comprises a rotatable drive 5 connected to a mounting surface 10 (see FIG. 16). Rotatable drive 5 may comprise any known mechanism converting electrical energy to rotational motion. In one embodiment rotatable drive 5 comprises a motor 15 connected to a rotatable shaft 20 (see FIG. 17).

Drive 5 may be connected to a top surface of mounting surface 10, and motor 15 and rotatable shaft 20 may project upwardly from a horizontal plane of mounting surface 10. Accordingly, rotatable drive 5, or rotatable shaft 20 thereof, is rotatable about a first axis that is perpendicular or substantially perpendicular to mounting surface 10.

Apparatus 2 further comprises a platform 25 for supporting a cell culture vessel. Platform 25 is connected to drive 5, and more particularly is connected to end 22 of rotatable drive 5, and still more particularly to end 22 of rotatable shaft 20 (see FIG. 17).

Platform 25 may be substantially planar to support a bottom surface of a cell culture vessel (not shown). Platform 25 may be any dimension provided that it can support at least one cell culture vessel on a top surface thereof. Many types of cell culture vessels are known in the art, and all are contemplated in this disclosure. Generally, the cell culture vessel can be any container capable of receiving cells for the culture thereof. By way of non-limiting example, the cell culture vessel may be a microplate, such as but not limited to a 6-well plate, a 12-well plate, a 24-well plate, or a 96-well plate, for example. Alternatively, the cell culture vessel may be a cell culture flask, such as but not limited to a T flask. In some embodiments where the cell culture vessel is a T flask, the platform may be appropriately dimensioned to support, for example, a T25 flask, a T75 flask, a T150 flask, a 175 flask, or a T225 flask. Alternatively, the cell culture vessel may be a cell culture dish, such as but not limited to a Petri dish, a 35 mm dish, a 10 mm dish, or larger.

In one embodiment, platform 25 is offsetedly connected to drive 5, or end 22 thereof. For instance, as previously described, drive 5 or end 22 thereof may define a first axis of rotation and the platform 25 may rotate about a second axis of rotation passing through a center of rotation of the platform 25. In some embodiments, drive 5 or end 22 may be coupled to platform 25 at a position offset from the center of rotation of platform 25. Where platform 25 is offsetedly connected to drive 5, platform 25 will have a wider orbit about the first axis (i.e. the axis of rotation of drive 5, or end 22 thereof) when compared to if drive 5 or end 22 thereof is coupled to the center or rotation of the platform 25.

In the same or different embodiments, platform 25 may also be indirectly connected to drive 5. In such embodiments, apparatus 1 may further comprise a spacer 27 intermediating attachment of platform 25 to drive 5. Spacer 27 may be any component that intermediates attachment of platform 25 to drive 5, while still being permissive of platform 25 rotating dependently or independently of rotatable drive 5. In preferred embodiments, spacer 27 is a bearing.

Figure 18:
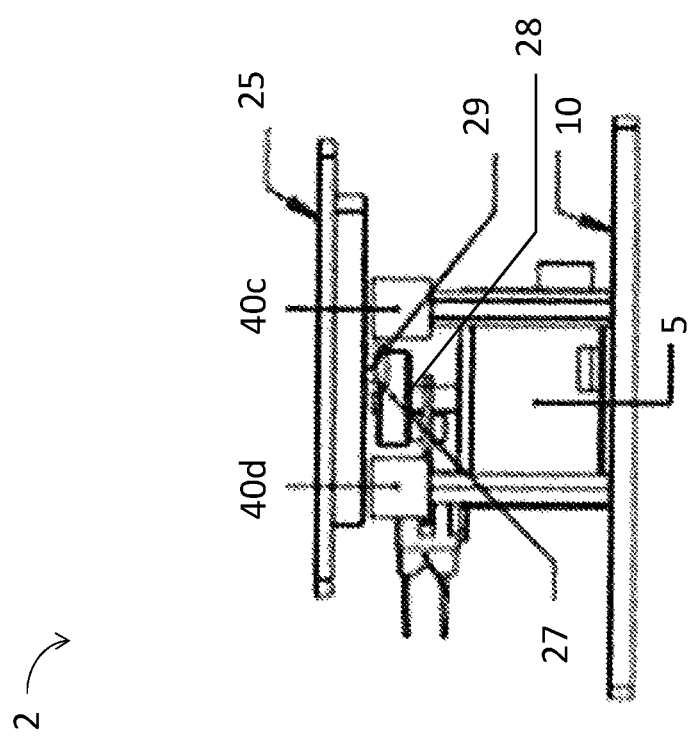
FIG. 18 shows a side view of the apparatus for dissociating one or more colonies present in a culture of cells.

In embodiments where platform 25 is indirectly and offsetedly connected to drive 5, spacer 27 may alternatively be referred to herein as an eccentric spacer. As may be seen in FIG. 18, spacer 27 may be connected at a first location 28 thereof to drive 5 and at a second location 29 thereof to platform 25. In a particular embodiment wherein spacer 27 is a bearing, drive 5 may be connected to a first race thereof (i.e. inner race) and platform 25 may be connected to a second race thereof (i.e. an outer race). Accordingly, first location 28 corresponds to the inner race and second location 29 corresponds to the second race.

In embodiments where spacer 27 is a bearing and platform 25 is connected to an outer race thereof, platform 25 is rotatable about a second axis that is offset from the first axis. In some embodiments, the second axis may pass through a center of rotation of the platform 25. In other embodiments, the second axis may pass through a point other than the center of rotation of the platform 25. The first axis and the second axis may be offset by any distance provided the geometries permit the operation of apparatus 1 and the interposition of the elements thereof, namely the one or more impact brackets and the one or more impact bumpers, which will be described in more detail below. In particular embodiments, the first axis (i.e. the first location) and the second axis (i.e. the second location) are offset by about 4 mm, by about 4.5 mm, by about 5 mm, by about 5.5 mm, by about 6 mm, by about 6.5 mm, by about 7 mm, by about 7.5 mm, by about 8 mm, by about 8.5 mm, by about 9 mm, by about 9.5 mm, or by about 10 mm.

In some embodiments, platform 25 may further comprise guide elements 30 that help position the cell culture vessel thereupon. Guide elements 30 may correspond to projections, such as but not limited to pins or ridges, rising upward from a top surface of platform 25. In addition to helping position the cell culture vessel on platform 25, guide elements 30 may also help secure the cell culture vessel upon platform 25 during operation of apparatus 2.

In embodiments where platform 25 is quadrilateral, guide elements 30 may be located on one or more corners of platform 25. In certain embodiments, guide elements 30 may be located on at least two corners of platform 25. In a more preferred embodiment, guide elements 30 may be located on all four corners of platform 25.

In embodiments where platform 25 is not quadrilateral, it would be straightforward to appropriately arrange guide elements 30 in a configuration that helps position, and optionally secure, the cell culture vessel to platform 25.

Apparatus 1 may further comprise one or more impact brackets 35 connected to platform 25. Impact brackets 35 may be connected to any part of platform 25, such as but not limited to one or more edges thereof or to an underside thereof. If the cell culture vessel has a larger footprint than the surface area of platform 25 it may be important to ensure that a top surface of impact brackets 35 does not protrude above the upper plane of platform 25.

Impact brackets 35 may be made of any material, but to minimize or resist excessive wear and noise, it may be desirable to manufacture impact brackets 35 out of a rubber or a rubber-like substance, and preferably a relatively dense rubber or rubber-like substance. Alternatively, impact brackets 35 may be made of a stronger and more durable material, such as but not limited to a metal or metalloid, and optionally capped with rubber or a rubber-like substance at the sites of impact.

In a specific embodiment, apparatus 2 comprises two impact brackets 35a and 35b. Impact brackets 35a and 35b may be connected to the underside or opposed edges of platform 25. Regardless of where impact brackets 35, including impact brackets 35a and 35b, are connected to platform 25, it is only important that they may be brought into contact with one or more impact bumpers 40 connected to mounting surface 10.

Impact bumpers 40 are generally coupled to an upper surface of the mounting surface 10 and extend axially from the mounting surface 10 towards an underside of the platform 25. In some embodiments, particularly when the impact brackets 35 are coupled to an underside of platform 25, impact bumpers 40 generally extend towards an underside of the platform 25 a distance that is less than a spacing between the mounting surface 10 and the platform 25.

Impact bumpers 40 may be made of any material, but to minimize or resist excessive wear and noise, it may be desirable to manufacture impact bumpers 40 out of rubber or a rubber-like substance, and preferably a relatively dense rubber or rubber-like substance. Alternatively, impact bumpers 40 may be made of a stronger and more durable material, such as but not limited to a metal or metalloid, and optionally capped with rubber or a rubber-like substance at the sites of impact.

In a specific embodiment, apparatus 2 comprises four impact bumpers 40a, 40b, 40c, and 40d arranged on mounting surface 10 to define a quadrilateral. Arrangement of impact bumpers 40a, 40b, 40c, and 40d may ensure that a travel of any one impact bracket, such as 35a or 35b, is bounded by two impact bumpers, such as 40c and 40d or 40a and 40b, respectively. Where the travel of the any one impact bracket is bounded by two impact bumpers, the travel of the impact brackets (and thus the platform) is constrained between the two impact bumpers.

Figure 19:
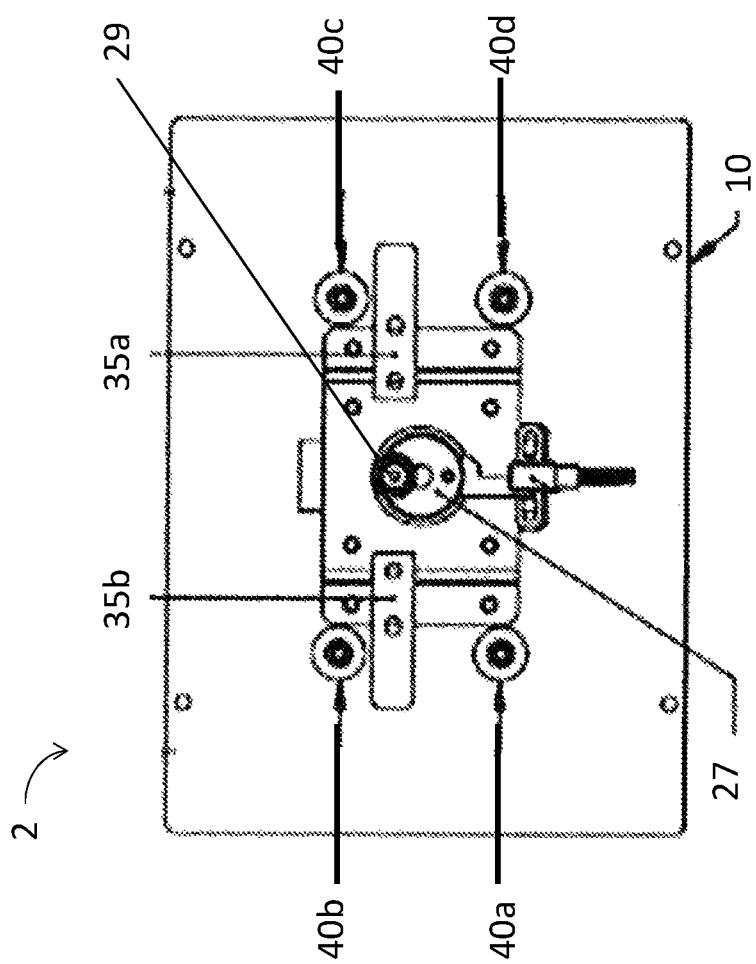
FIG. 19 shows a top view of the apparatus for dissociating one or more colonies present in a culture of cells. For illustrative purposes the platform is not shown, while the impact brackets that are generally connected thereto are depicted.

With reference to FIG. 19, an exemplary arrangement of impact brackets 35a and 35b and impact bumpers 40a, 40b, 40c, and 40d is shown. By way of illustration only, when platform 25 (not shown in FIG. 19) rotates in a given direction under the direct influence of drive 5, impact bracket 35a is collided with impact bumper 40c. By virtue of spacer 27, bracket 35a may rebound toward and potentially into contact with impact bumper 40d independently of a rotation of drive 5. The same dynamics occur in respect of impact bracket 35b and impact bumpers 40a and 40b.

Thus, the one or more impact bumpers 40 are connected to mounting surface 10 and are contactable by one or more impact brackets 35 as platform 25 rotates under the influence of drive 5. Repeated collision of the one or more impact brackets 35 with the one or more impact bumpers 40 transmits a force upon platform 25, and to any cell culture vessel thereon, including the contents contained therein. Such an agitating or percussive force may cause the one or more colonies of cultured cells contained in the cell culture vessel to dissociate into smaller units, such as but not limited to clumps or clusters of cells.

Apparatus 2 may further comprise a controller that regulates an output of drive 5. By manipulating the controller, a direction of rotation of drive 5, a velocity of rotation of drive 5; and an acceleration of rotation of drive 5 is adjustable. In specific embodiments, the direction of rotation of drive 5 may be clockwise. In other embodiment, the direction of rotation of drive 5 may be counterclockwise. In a more specific embodiment, the direction of rotation of drive 5 may be clockwise or counterclockwise. In a still more specific embodiment, the direction of rotation of drive 5 may oscillate between clockwise and counterclockwise.

Apparatus 2 may further comprise sensors such as an accelerometer or optical flag sensor to receive feedback on the operation of the apparatus.

Apparatus 2 may further comprise a home sensor to provide an orientation of the platform.

Methods of Using the Apparatus

In another aspect of this disclosure, apparatus 2 may be used in methods of dissociating one or more colonies in a culture of cells. In a non-limiting embodiment, the culture of cells may be the culture of pluripotent stem cells comprised in one or more colonies. In a more specific non-limiting embodiment, the one or more colonies in a culture of cells may be one or more undifferentiated colonies in a culture of pluripotent stem cells, and optionally wherein the pluripotent stem cells are human.

In other aspects of this disclosure, apparatus 2 may be used in methods of distributing cells seeded in a culture medium within a well of a cell culture vessel, or in methods of coating a well of a cell culture vessel with a coating material, such as an extracellular matrix.

The methods that follow rely on providing an apparatus in accordance with this disclosure and positioning a cell culture vessel containing one or more colonies in a culture of cells upon the apparatus. In certain embodiments securing the cell culture vessel to the stage may be desirable. For example, the cell culture vessel may be secured to the stage through co-operation of the cell culture vessel and the guide elements.

In some embodiments, the culture of cells may have been incubated in the presence of a detaching solution, which may or may not have subsequently been removed, deactivated or neutralized. Using a detaching solution may be desirable when the one or more colonies of cultured cells are directly or indirectly adhered to a well bottom of the cell culture vessel. Common examples of detaching solutions include ReLeSR™ (STEMCELL Technologies Inc.) and STEMdiff™ Neural Rosette Selection Reagent (STEMCELL Technologies Inc.). With reference to detaching solutions in general, and to ReLeSR™ and STEMdiff™ Neural Rosette Selection Reagent specifically, such detaching solutions may be added to an appropriate culture of cells for a brief period (e.g. from 1 to 15 minutesand subsequently removed prior to incubating the culture of cells for a further period of time. Following such incubation, some or all of the colonies may have detached from the well bottom or have become prone to detaching from the well bottom in response to minimal force.

In other embodiments, the culture of cells may have been incubated in the presence of a dissociation solution, which may or may not have subsequently been removed, deactivated or neutralized. Using dissociation solutions may be desirable when working with cells that grow as a monolayer. A common example of a dissociation solution is trypsin. The skilled person will be aware that for certain cell lines or cell types excessive exposure to a dissociation solution may completely dissociate the one or more colonies in a culture of cells and/or possibly damage the culture of cells.

In still other embodiments, the culture of cells may be positioned upon the apparatus while incubating the culture of cells in the presence of the detaching or dissociation solution. In such embodiments, the one or more colonies in the culture of cells may be simultaneously dissociated using the apparatus of this disclosure, or immediately dissociated using the apparatus of this disclosure after a sufficient incubation period. In some embodiments, certain detaching or dissociation solutions may work optimally at a given temperature (i.e. 37° C. or higher). In some embodiments, it may be desirable to provide a heating element to the apparatus described herein for heating the platform and/or an enclosure surrounding the apparatus or the platform.

Regardless of the foregoing detaching or dissociation practices, after the culture of cells has incubated for a sufficient period of time, the one or more colonies in the culture of cells may be ready for dissociation into smaller units using an apparatus as described in this disclosure. As described above, rotating the platform under the influence of the drive causes the one or more impact brackets to come into contact with the one or more impact bumpers, thereby transmitting a dissociative force to the one or more colonies in the culture of cells.

In some embodiments adjusting a speed of rotation of the drive, and therefore a speed of rotation of the platform, may be desirable to optimally dissociate the one or more colonies in the culture of cells. By adjusting the speed of the rotation of the drive upward the impact frequency is increased. Likewise, adjusting the speed of the rotation of the drive downward the impact frequency is decreased. The skilled person will realize that an appropriate impact frequency may depend on the particular cell line or cell type cultured.

In some embodiments, adjusting a direction of rotation of the drive may be desirable to optimally dissociate the one or more colonies in the culture of cells. In one embodiment, rotating the stage is in a clockwise direction. In another embodiment, rotating the stage is in a counterclockwise direction. In a still other embodiment, rotating the stage is in a clockwise or a counterclockwise direction.

In a still further embodiment, rotating the stage may comprise oscillating between a clockwise and a counterclockwise direction. In embodiments comprising oscillating a direction of rotation of the stage in a clockwise and a counterclockwise direction, oscillating may include a delay of less than five seconds between rotating in the clockwise and counterclockwise direction. In a more specific embodiment comprising oscillating a direction of rotation of the stage in a clockwise and a counterclockwise direction, oscillating may include a delay of less than 1 second between rotating in the clockwise and counterclockwise direction. In a still more specific embodiment comprising oscillating a direction of rotation of the stage in a clockwise and a counterclockwise direction, oscillating may include a delay of about 0.5 milliseconds or less between rotating in the clockwise and counterclockwise direction.

In embodiments comprising adjusting a speed, direction or acceleration of rotation of the drive, such operations may be effected by a controller, as described hereinabove. Thus, certain embodiments of the methods disclosed herein may further comprise controlling a speed, direction or acceleration of rotation of the drive using a controller.

Some embodiments of the methods disclosed herein are specifically directed to dissociating one or more undifferentiated colonies of pluripotent stem cells, such as but not limited to human pluripotent stem cells. In such methods, it may be desirable to exploit the preference of certain detaching solutions, such as but not limited to ReLeSR™, for selectively detaching undifferentiated colonies of pluripotent stem cells. Accordingly, methods that pair selective detaching solutions, such as but not limited to ReLeSR™, with the use of an apparatus of this disclosure may advantageously select for desired cell types simultaneously with dissociating the desired one or more colonies present in a culture of cells into smaller units.

In one embodiment of dissociating one or more undifferentiated colonies of human pluripotent stem cells in a culture of cells, a detaching solution, such as but not limited to ReLeSR™, may weaken the attachment of undifferentiated colonies of human pluripotent stem cells to a well bottom of a well of a cell culture vessel. Upon adding a volume of solution, such as but not limited to a cell culture medium, to the well some or all of the one or more colonies of human pluripotent stem cells may detach from the well bottom and become suspended in the solution. Any remaining undifferentiated colonies of human pluripotent stem cells attached to the well bottom may become detached from well bottom upon rotating the platform under the influence of the drive and colliding repeatedly the one or more impact brackets with the one or more impact bumpers. Simultaneous with the selection of the one or more undifferentiated colonies of the human pluripotent stem cells, such colonies are broken down into smaller units (i.e. clumps) as they collide with one another and against the well walls of the cell culture vessel.

In an alternative embodiment, such as but not limited to during a differentiation experiment, it may be desirable to select for one or more differentiated colonies of pluripotent stem cells. Following the same process as described above, the detached and dissociated pluripotent stem cells may be aspirated and discarded from the well of the cell culture vessel to yield the (differentiated) colonies of interest attached to the well bottom for further culture or processing.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

What is claimed is:

1. An automated system for adaptively passaging a culture of cells in a cell culture medium within a cell culture vessel, the automated system comprising:
    an imaging station comprising a camera for capturing one or more images of the culture of cells at a first time point and at one or more subsequent time points;
    a pipette module having one or more pipettes for drawing a fluid from the cell culture vessel through a pipette tip mateable with an end of the one or more pipettes;
    a liquid dispenser station spaced apart from the pipette module and in fluid communication with more than one solution reservoir, the liquid dispenser station comprising more than one conduit respectively in fluid communication with a separate one of the more than one solution reservoirs, wherein a solution is dispensed from the liquid dispenser station in bulk into the cell culture vessel;
    a handling module having a pair of opposable arms for gripping and transporting the cell culture vessel or a lid thereof or a daughter cell culture vessel or a lid thereof within the automated system; and
    at least one processor in communication with the imaging station, the pipette module, the liquid dispenser station, and the handling module, the processor configured to:
    receive the one or more images from the imaging station;
    based on the one or more images received from the imaging station, calculate one or more characteristics of the culture of cells; and
    execute an automated passaging protocol to passage the culture of cells, the protocol including coordinating operation of the pipette module, the liquid dispenser station and the imaging station based on comparing the calculated one or more characteristics of the culture of cells to:
    a) a learned threshold level for the one or more characteristics; or
    b) an inputted threshold level for the one or more characteristics;
    wherein:
    the one or more characteristics calculated in respect of the culture of cells in the cell culture vessel and a second culture of cells in a second cell culture vessel is different at the first time point or at the one or more subsequent time points and the different one or more characteristics become more consistent between the culture of cells in the cell culture vessel and the second culture of cells in the second cell culture vessel during a subsequent passage; and
    wherein the culture of cells and the second culture of cells are the same type of cells.

2. The automated system according to claim 1, wherein the one or more characteristics includes:
    a) a measure of a confluence of the culture of cells;
    b) a measure of a morphology of cells or colonies of the culture of cells;
    c) a measure of differentiation of cells or colonies of the culture of cells;
    d) a measure of colony size distribution of the culture of cells;
    e) a measure of the change of a), b), c), or d) from the first time point to the one or more subsequent time points; or
    f) a measure of a) relative to b), c) or d), a measure of b) relative to a), c), or d), a measure of c) relative to a), b), or d), or a measure of d) relative a), b), or c).

3. The automated system according to claim 2, wherein the learned or the inputted threshold level is:
    i. for a), between 30-90% for cell or colony confluence;
    ii. for b), between ±30% of a control culture;
    iii. for c), between 0 to 30% of a control culture in a maintenance protocol or between 50% to 100% of a control culture in a differentiation protocol; or
    iv. for d), within 15% of a mean colony size distribution of a control culture, or a subfraction thereof.

4. The automated system according to claim 1, further comprising a stage comprising a platform for supporting the cell culture vessel, the stage movable in a first plane along a first axis or a second axis, or both.

5. The automated system according to claim 4, wherein the stage or a subcomponent thereof pivots about an edge thereof along a third axis.

6. The automated system according to claim 1, further comprising a refrigeration station to store one or more of the more than one solution reservoirs and a waste reservoir, wherein the more than one solution reservoirs, the refrigeration module and the waste reservoir are external of an enclosure housing at least the stage, the imaging station, the pipette module, the liquid dispenser station, and the handling module.

7. The automated system according to claim 6, wherein the waste reservoir is in fluid communication with a waste trough within the enclosure.

8. The automated system according to claim 7, wherein the waste trough is coated with a hydrophobic coating.

9. The automated system according to claim 1, further comprising one or more load sensors, wherein the one or more load sensors are configured to i) detect and report on a mass of a load on the imaging station, on the stage, or in the more than one solution reservoirs, and ii) trigger an alert when the mass of the load is different than expected.

10. An automated method for adaptively passaging a culture of cells, comprising:
    providing the culture of cells in a cell culture medium within a cell culture vessel, wherein the cell culture medium is dispensed in bulk into the cell culture vessel from a liquid dispenser station including more than one conduit and wherein each conduit is in fluid communication with a separate one of the more than one solution reservoirs and wherein the liquid dispenser station is spaced apart from a pipette module;
    capturing by a camera one or more images of the culture of cells at a first time point and at one or more subsequent time points;
    transforming the one or more images to contrast the culture of cells from a background;
    calculating by at least one processor communicatively coupled to the camera one or more characteristics of the culture of cells based on the transformed one or more images; and executing by the at least one processor an automated passaging protocol based on comparing the calculated one or more characteristics of the culture of cells to:
a) a learned threshold level for the one or more characteristics; or
b) a pre-determined threshold level for the one or more characteristics;

wherein:

the one or more characteristics calculated in respect of the culture of cells in the cell culture vessel and a second culture of cells in a second cell culture vessel is different at the first time point or at the one or more subsequent time points and the different one or more characteristics become more consistent between the culture of cells in the cell culture vessel and the second culture of cells in the second cell culture vessel during a subsequent passage; and wherein the culture of cells and the second culture of cells are the same type of cells.

11. The automated system according to claim 10, wherein the one or more characteristics includes:
   a) a measure of the confluence of the culture of cells;
   b) a measure of the morphology of cells or colonies of the culture of cells;
   c) a measure of the differentiation of cells or colonies of the culture of cells;
   d) a measure of colony size distribution of the culture of cells;
   e) a measure of the change of a), b), c), or d) from the first time point to the one or more subsequent time points; or
   f) a measure of a) relative to b), c) or d), a measure of b) relative to a), c), or d), a measure of c) relative to a), b), or d), or a measure of d) relative a), b), or c).

12. The automated system according to claim 11, wherein the learned or the inputted threshold level is:
   i. for a), between 30-90% for cell or colony confluence;
   ii. for b), between ±30% of a control culture;
   iii. for c), between 0 to 30% of a control culture in a maintenance protocol or between 50% to 100% of a control culture in a differentiation protocol; or
   iv. for d), within 15% of a mean colony size distribution of a control culture, or a subfraction thereof.

13. The automated method according to claim 10, further comprising obtaining a suspension of cells from the culture of cells and seeding some or all of the suspension of cells in a daughter cell culture vessel.

14. The automated method according to claim 13, wherein prior to seeding in the daughter cell culture vessel the suspension of cells is passed through a first pipette tip to dissociate the culture of cells into a single cell suspension or a plurality of clumps having an average diameter not exceeding a bore diameter of the first pipette tip.

15. The automated method according to claim 13, wherein obtaining the suspension of cells includes aspirating the cell culture medium from the cell culture vessel and contacting the culture of cells in the cell culture vessel with a detachment solution.

16. The automated method according to claim 15, wherein the detachment solution is a fractionation solution, and the fractionation solution selectively detaches either a first population of differentiated cells or a second population of undifferentiated cells from a wall of the cell culture vessel.

17. The automated method according to claim 10, wherein the culture of cells are pluripotent stem cells.

18. The automated method according to claim 17, wherein the pluripotent stem cells are human pluripotent stem cells.

19. The automated method according to claim 17, wherein the pluripotent stem cells are passaged as clumps.

20. The automated system according to claim 1, wherein the pipette module and the handling module are comprised in a carriage.

21. The automated system according to claim 4, wherein the stage at least partially underlies the liquid dispenser station and the imaging station.

* * * * *